United States Patent
Nostrand et al.

(10) Patent No.: US 11,399,534 B2
(45) Date of Patent: Aug. 2, 2022

(54) TECHNIQUES FOR PROVIDING A BROAD-BAND ULTRASONIC TRANSDUCER DEVICE USING A PLURALITY OF NARROW-BAND TRANSDUCER ARRAYS AND A METHOD OF WILDLIFE DETERRENCE USING SAME

(71) Applicant: NRG SYSTEMS, INC., Hinesburg, VT (US)

(72) Inventors: Thomas J. Nostrand, Hinesburg, VT (US); Cody Spiegel, Washington, VT (US); Dale E. Williams, Winooski, VT (US); Junda Zhu, South Burlington, VT (US)

(73) Assignee: NRG SYSTEMS, INC., Hinesburg, VT (US)

( * ) Notice: Subject to any disclaimer, the term of this patent is extended or adjusted under 35 U.S.C. 154(b) by 1172 days.

(21) Appl. No.: 15/925,186

(22) Filed: Mar. 19, 2018

(65) Prior Publication Data
US 2018/0206477 A1 Jul. 26, 2018

Related U.S. Application Data

(63) Continuation of application No. PCT/US2016/060330, filed on Nov. 3, 2016.
(Continued)

(51) Int. Cl.
*A01M 29/18* (2011.01)
*B06B 1/02* (2006.01)
(Continued)

(52) U.S. Cl.
CPC .............. *A01M 29/18* (2013.01); *A61N 7/00* (2013.01); *B06B 1/0269* (2013.01);
(Continued)

(58) Field of Classification Search
CPC .... A01M 29/18; B06B 1/0269; B06B 1/0622; B06B 2201/75; B06B 1/0614; B06B 1/0603; G01N 29/34
See application file for complete search history.

(56) References Cited

U.S. PATENT DOCUMENTS

| | | |
|---|---|---|
| 3,872,472 A | 3/1975 | Moschgat |
| 3,893,106 A | 7/1975 | Schulein |

(Continued)

FOREIGN PATENT DOCUMENTS

| | | |
|---|---|---|
| DE | 9312530 | 10/1993 |
| DE | 10051784 | 8/2002 |

(Continued)

OTHER PUBLICATIONS

German Office Action dated May 10, 2019 in corresponding German Patent Application No. 11 2016 005 038.0.
(Continued)

*Primary Examiner* — Ian J Lobo
(74) *Attorney, Agent, or Firm* — Grossman, Tucker, Perreault & Pfleger, PLLC

(57) ABSTRACT

A broadband ultrasonic transducer device (UTD) is disclosed that utilizes a plurality of narrow-band piezo electric elements grouped into single-frequency sub-arrays to provide a relatively simple, highly-reliable deterrent unit (DU) capable of emitting ultrasonic energy over a wide coverage area and at a sound pressure level that meets or exceeds other DU approaches. In an embodiment, the broadband UTD includes a housing portion configured to couple to a plurality of piezo sub-array plates. Each piezo sub-array plate includes a plurality of pockets or cavities to receive respective narrow-band (e.g., 1-3 kHz) piezo electro transducer elements with characteristics, e.g., geometries and material composition, that cause each to emit ultrasonic energy at a particular resonant frequency. A controller of the
(Continued)

UTD implements a control scheme to emit ultrasonic energy in a plurality of output modes including a white noise node and a single-frequency mode for deterrence applications.

20 Claims, 17 Drawing Sheets

Related U.S. Application Data

(60) Provisional application No. 62/250,240, filed on Nov. 3, 2015.

(51) Int. Cl.
  *B06B 1/06* (2006.01)
  *G01N 29/34* (2006.01)
  *A61N 7/00* (2006.01)

(52) U.S. Cl.
  CPC .......... *B06B 1/0603* (2013.01); *B06B 1/0614* (2013.01); *B06B 1/0622* (2013.01); *G01N 29/34* (2013.01); *B06B 2201/75* (2013.01)

(56) References Cited

U.S. PATENT DOCUMENTS

| | | | |
|---|---|---|---|
| 4,442,715 A | 4/1984 | Brisken et al. | |
| 4,608,993 A | 9/1986 | Albert | |
| 4,616,351 A | 10/1986 | Hall | |
| 5,598,379 A | 1/1997 | Malleolo | |
| 6,166,996 A | 12/2000 | Grossom et al. | |
| 6,250,255 B1 | 6/2001 | Lenhardt et al. | |
| 6,653,760 B1 | 11/2003 | Goodson | |
| 7,173,534 B1 | 2/2007 | Markham et al. | |
| 8,472,651 B2 | 6/2013 | Pompei | |
| 8,567,131 B2 | 10/2013 | Ollgaard | |
| 8,576,174 B2 * | 11/2013 | Cruz-Hernandez | B06B 1/0603 345/169 |
| 8,598,998 B2 | 12/2013 | Vassilev et al. | |
| 8,723,399 B2 * | 5/2014 | Sammoura | B06B 1/0603 310/322 |
| 8,737,170 B2 | 5/2014 | Kasper | |
| 8,934,650 B1 | 1/2015 | Norris et al. | |
| 8,938,931 B2 | 1/2015 | Ollgaard | |
| 9,125,394 B2 | 9/2015 | Kinzie et al. | |
| 9,217,412 B2 | 12/2015 | Blake et al. | |
| 9,261,081 B2 | 2/2016 | Ollgaard | |
| 9,474,265 B2 | 10/2016 | Duncan et al. | |
| 9,693,548 B2 | 7/2017 | Swaddle et al. | |
| 2002/0047496 A1 | 4/2002 | Wierach | |
| 2003/0058740 A1 | 3/2003 | Jincks | |
| 2004/0195478 A1 | 10/2004 | Baldasari | |
| 2005/0085730 A1 | 4/2005 | Flesch et al. | |
| 2005/0162978 A1 | 7/2005 | Lima | |
| 2006/0233049 A1 | 10/2006 | Cilliers | |
| 2009/0034369 A1 | 2/2009 | Hill | |
| 2010/0016727 A1 | 1/2010 | Rosenberg | |
| 2011/0190669 A1 | 8/2011 | Mi et al. | |
| 2011/0215585 A1 | 9/2011 | Caires | |
| 2011/0295123 A1 | 12/2011 | Feleppa | |
| 2013/0050400 A1 | 2/2013 | Stiesdal et al. | |
| 2013/0077446 A1 | 3/2013 | Kasper | |
| 2013/0100776 A1 * | 4/2013 | Karl | G01S 7/521 367/137 |
| 2013/0131495 A1 | 5/2013 | Konofagou et al. | |
| 2013/0239876 A1 | 9/2013 | Kocker-Kunz | |
| 2013/0249693 A1 | 9/2013 | Neal et al. | |
| 2013/0293065 A1 * | 11/2013 | Hajati | B06B 1/0629 310/334 |
| 2013/0336775 A1 | 12/2013 | Blake et al. | |
| 2014/0117812 A1 * | 5/2014 | Hajati | B06B 1/0629 310/314 |
| 2014/0144390 A1 | 5/2014 | Duncan et al. | |
| 2014/0169968 A1 | 6/2014 | Hedeen et al. | |
| 2014/0261151 A1 | 9/2014 | Ronning | |
| 2014/0269204 A1 | 9/2014 | Hajati | |
| 2014/0352631 A1 | 12/2014 | Swaddle et al. | |
| 2014/0377061 A1 | 12/2014 | Caruso et al. | |
| 2015/0010399 A1 | 1/2015 | Bahat et al. | |
| 2015/0230450 A1 | 8/2015 | Norris | |
| 2016/0076519 A1 | 3/2016 | Blake et al. | |
| 2016/0366875 A1 | 12/2016 | Green et al. | |
| 2017/0000106 A1 | 1/2017 | Duncan | |

FOREIGN PATENT DOCUMENTS

| | | |
|---|---|---|
| DE | 102012003495 | 8/2013 |
| DE | 102015224763 | 6/2017 |
| EP | 2818702 | 12/2014 |
| FR | 2342658 | 10/1983 |
| GB | 1517493 | 7/1978 |
| GB | 2166277 | 4/1986 |
| GB | 2211649 | 7/1989 |
| WO | 8602526 | 5/1986 |
| WO | 2004093537 | 11/2004 |
| WO | 2011027093 A1 | 3/2011 |
| WO | 2013144676 | 10/2013 |
| WO | 2017079435 | 5/2017 |
| WO | 2017097478 | 6/2017 |

OTHER PUBLICATIONS

Minoru Toda; "New Type of Matching Layer for Air-Coupled Ultrasonic Transducers"; IEEE Transactions on Ultrasonics, Ferroelectrics, and Frequency Control, vol. 49, No. 7, Jul. 2002; pp. 972-979.

T.E. G. Alvarez-Arenas; "Acoustic Impedance Matching of Piezoelectric Transducers to the Air"; IEEE Transactions on Ultrasonics, Ferroelectrics, and Frequency Control; vol. 51, Issue 5, May 2004; pp. 624-633.

International Search Report and Written Opinion dated Jul. 1, 2019 in PCT Patent Application No. PCT/US2019/026798.

International Search Report and Written Opinion issued in PCT/US2016/060330, dated Jan. 19, 2017, 11 pages.

Frontier Wind; "Rotor-Mounted Bat Impact Mitigation System," Wind Energy Technologies Office Peer Review; US Dept of Energy; Feb. 2017; pp. 1-14; website www.eere.energy.gov.

\* cited by examiner

TECHNIQUES FOR PROVIDING A BROAD-BAND ULTRASONIC TRANSDUCER DEVICE USING A PLURALITY OF NARROW-BAND TRANSDUCER ARRAYS AND A METHOD OF WILDLIFE DETERRENCE USING SAME

CROSS-REFERENCE TO RELATED APPLICATIONS

This application is a continuation of International Patent Application No. PCT/US2016/60330, filed Nov. 3, 2016, designating the U.S. and claiming the benefit of U.S. Provisional Patent Application Ser. No. 62/250,240, filed Nov. 3, 2015, the entire disclosures of which are incorporated herein by reference.

TECHNICAL FIELD

The present disclosure generally relates to ultrasonic transducer devices, and more particularly, to a broadband ultrasonic transducer device having a plurality of piezo electric transducer sub-arrays for use in deterrence applications.

BACKGROUND INFORMATION

Many forms of renewable energy, such as wind turbines, endanger wildlife such as bats and other animals that have habitats in close proximity. Some solutions to deterring wildlife includes using ultrasonic transducer devices (UTDs) that output specific frequencies at a sufficient sound pressure level (SPL) to cause animals to avoid dangerous areas. For example, a wind turbine structure may include a plurality of UTDs disposed at strategic locations to prevent bats from being killed or injured by turbine blades. One such approach includes using broadband electro-static type ultrasonic (ETU) transducers. Such ETU transducer devices are often not reliable and subject to short MTBFs in outdoor and industrial environments.

BRIEF DESCRIPTION OF THE DRAWINGS

These and other features and advantages will be better understood by reading the following detailed description, taken together with the drawings wherein.

DETAILED DESCRIPTION

Figure 12A:
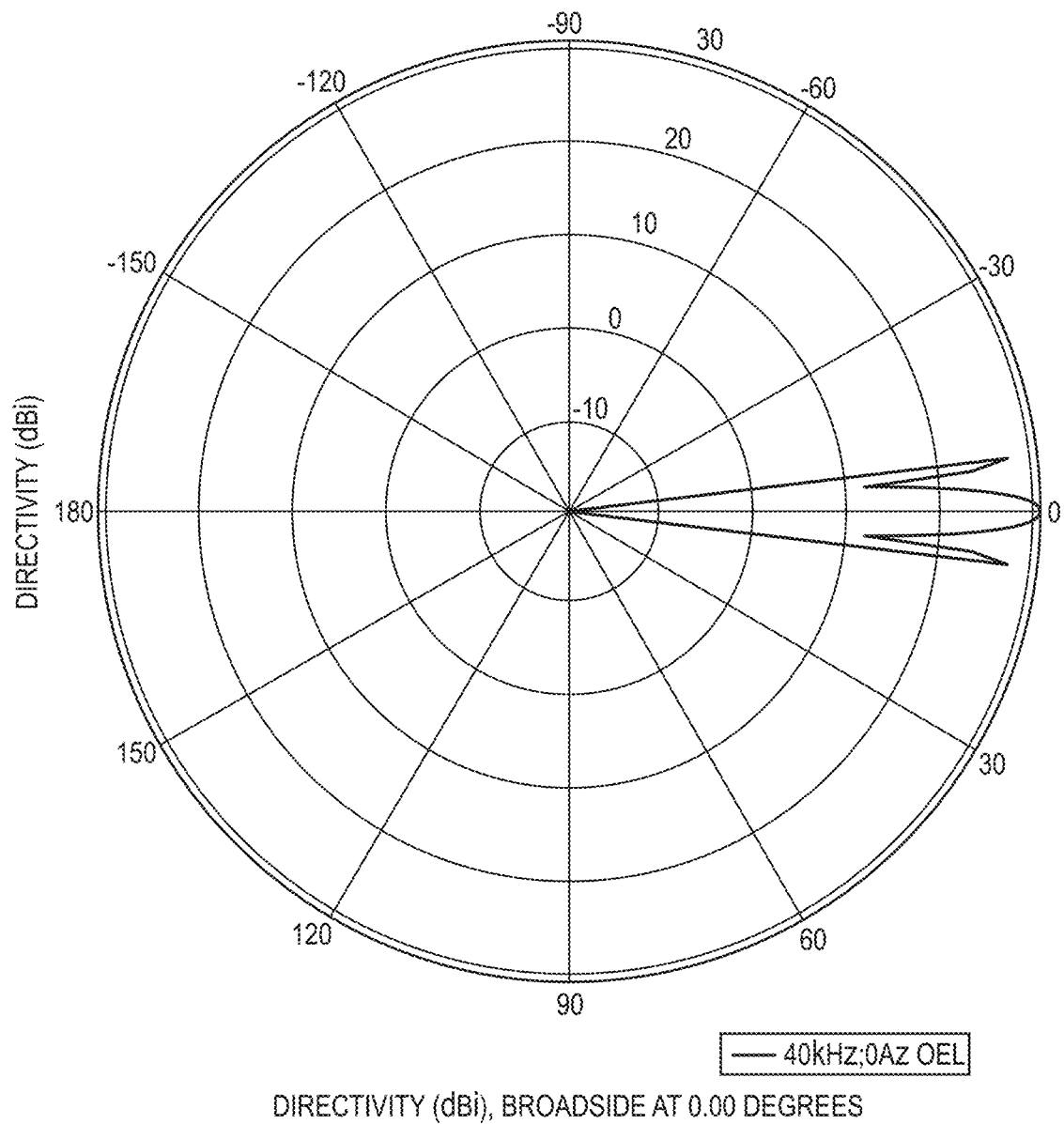
FIG. 12A shows a polar plot that illustrates a ½ beam width for an electrostatic transducer element that is utilized in some deterrent units.
Figure 12B:
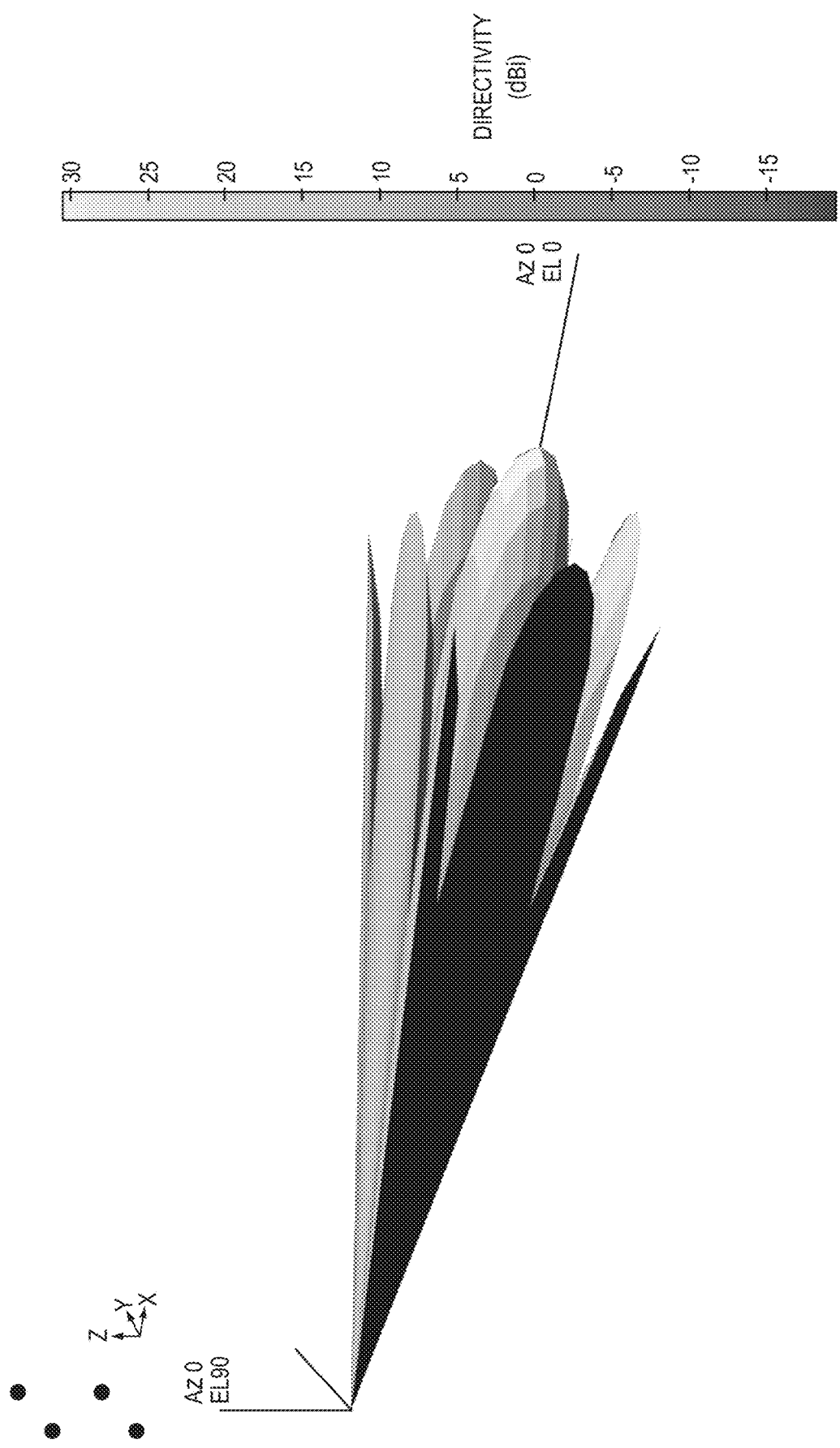
FIG. 12B illustrates a three-dimensional plot for the ½ beam width for an electrostatic transducer element.

As discussed above, broadband ETU transducers operate poorly in environments that expose the ETU transducer devices to dust, moisture and other environmental conditions. Some broadband ETU transducers include additional protections to increase reliability, e.g., secondary sealed housings, but these additional protections increase design complexity and cost. In addition, ETU transducers include a generally limited beam width, which requires a relatively large number of devices to ensure a sufficient area of protection without dead zones. For example, FIG. 12A shows a polar plot for one example broadband ETU transducer and illustrates a ±7.5 degree ½ beam angle radiation pattern. FIG. 12B illustrates the same ±7.5 degree ½ beam angle radiation pattern in a three-dimensional plot. These limitations significantly limit the development of inexpensive, robust and reliable deterrent unit (DU) devices.

Thus, in accordance with an embodiment, a broadband ultrasonic transducer device (UTD) is disclosed that utilizes a plurality of narrow-band piezo electric elements grouped into single-frequency sub-arrays to provide a relatively simple, highly-reliable deterrent unit (DU) capable of emitting ultrasonic energy over a wide coverage area at a SPL that meets or exceeds other DU approaches. In an embodiment, the broadband UTD includes a housing portion configured to couple to a plurality of piezo sub-arrays or piezo sub-array plates. Each piezo sub-array plate includes a plurality of machined pockets or cavities to receive respective narrow-band (e.g., 1 kHz-3 kHz) piezo electro transducer elements with characteristics, e.g., geometries, material composition, that cause each piezo sub-array plate to emit ultrasonic energy at a nominal resonant frequency. Each piezo sub-array plate therefore emits at a single-frequency, with each of the associated piezo elements, in a general sense, amplifying that single-frequency. The housing portion of the broadband UTD includes an array of the piezo sub-array plates to provide broadband emission capabilities, which is particularly advantageous in deterrent unit (DU) applications.

One such example bandwidth of interest particularly well suited for wildlife deterrence is 20 kHz to 60 kHz, which is the range of frequency that characterize white noise. White noise, as generally referred to herein, refers to a randomly generated signal with a constant power spectral density that includes a finite bandwidth. The present disclosure has also identified that a constant, or single-frequency, output may also sufficiently deter wildlife even with nulls or gaps between frequencies. A broadband UTD configured in accordance with the present disclosure may implement a control scheme to decide when to drive each piezo sub-array plate to emit ultra-sonic energy in a particular pattern to, for example, approximate white noise or to drive each piezo sub-array plate at a single frequency. Note a broadband UTD configured in accordance with the present disclosure is not necessarily limited to a frequency in the range of 20 kHz and 60 kHz, and may be configured to output other frequencies up to and exceeding 100 kHz, for instance, depending on a desired configuration.

In the case of white noise, which may be referred to as the white noise mode, the broadband UTD may drive N number of piezo sub-array plates at a given instance in time, with each piezo sub-array plate being driven to emit a randomly selected frequency for a relatively short period of time, e.g., a predetermined dwell time. In the case of single-frequency, which may be referred to as the single-frequency mode, the broadband UTD may simultaneously drive each piezo sub-array plate at an associated frequency for a brief period of time, e.g., a predetermined dwell time. In this case, the net effect over a period of time T results in a maximum SPL emitted by the broadband UTD which has been found to perform substantially similar to that of white noise in deterrent applications. In some cases, the broadband UTD may dynamically switch between white noise modes and single-frequency modes during operation, depending on a desired configuration.

Figure 13A:
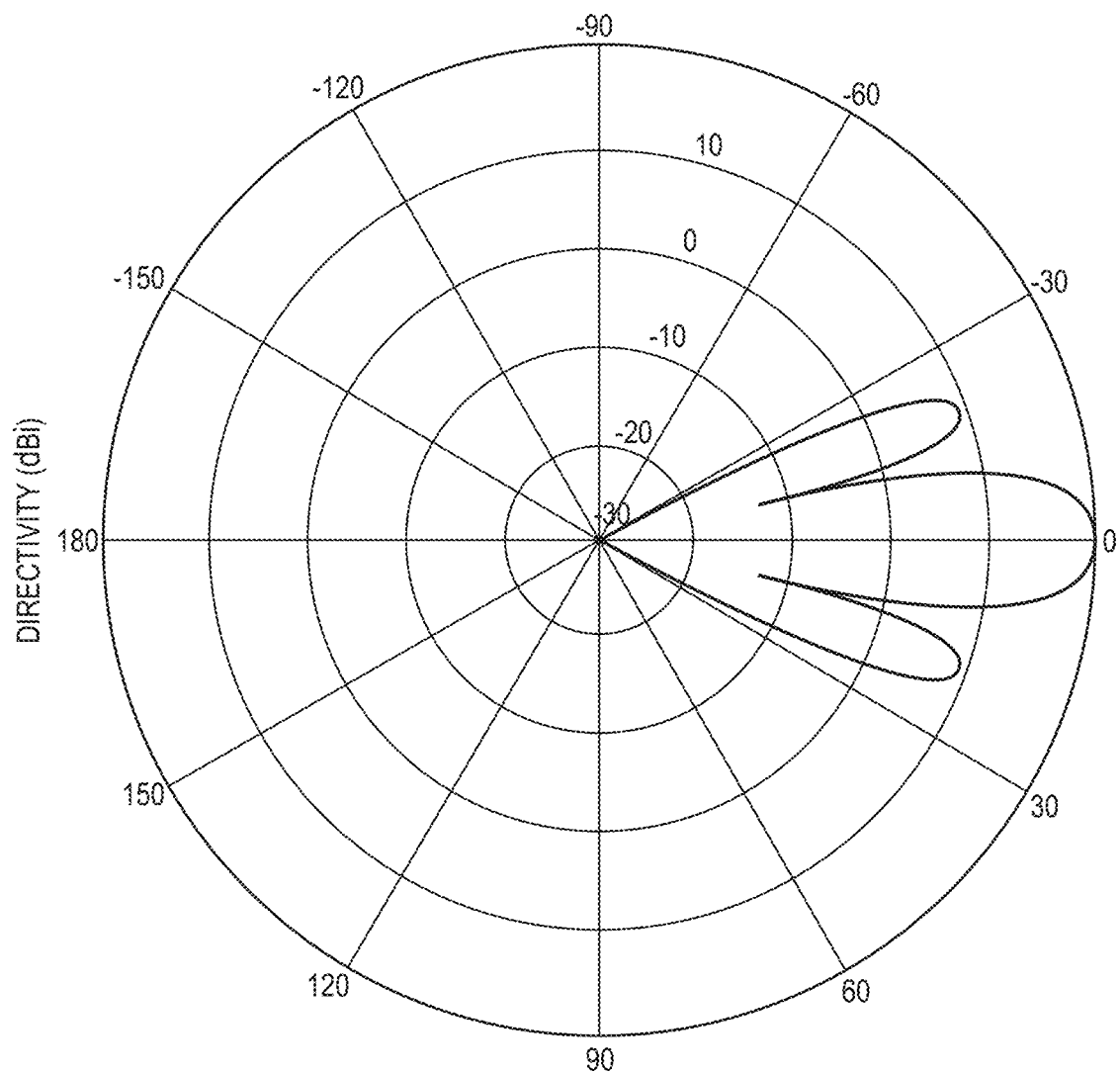
FIG. 13A shows a polar plot that illustrates a ½ beam width for a UTD configured in accordance with an embodiment of the present disclosure.
Figure 13B:
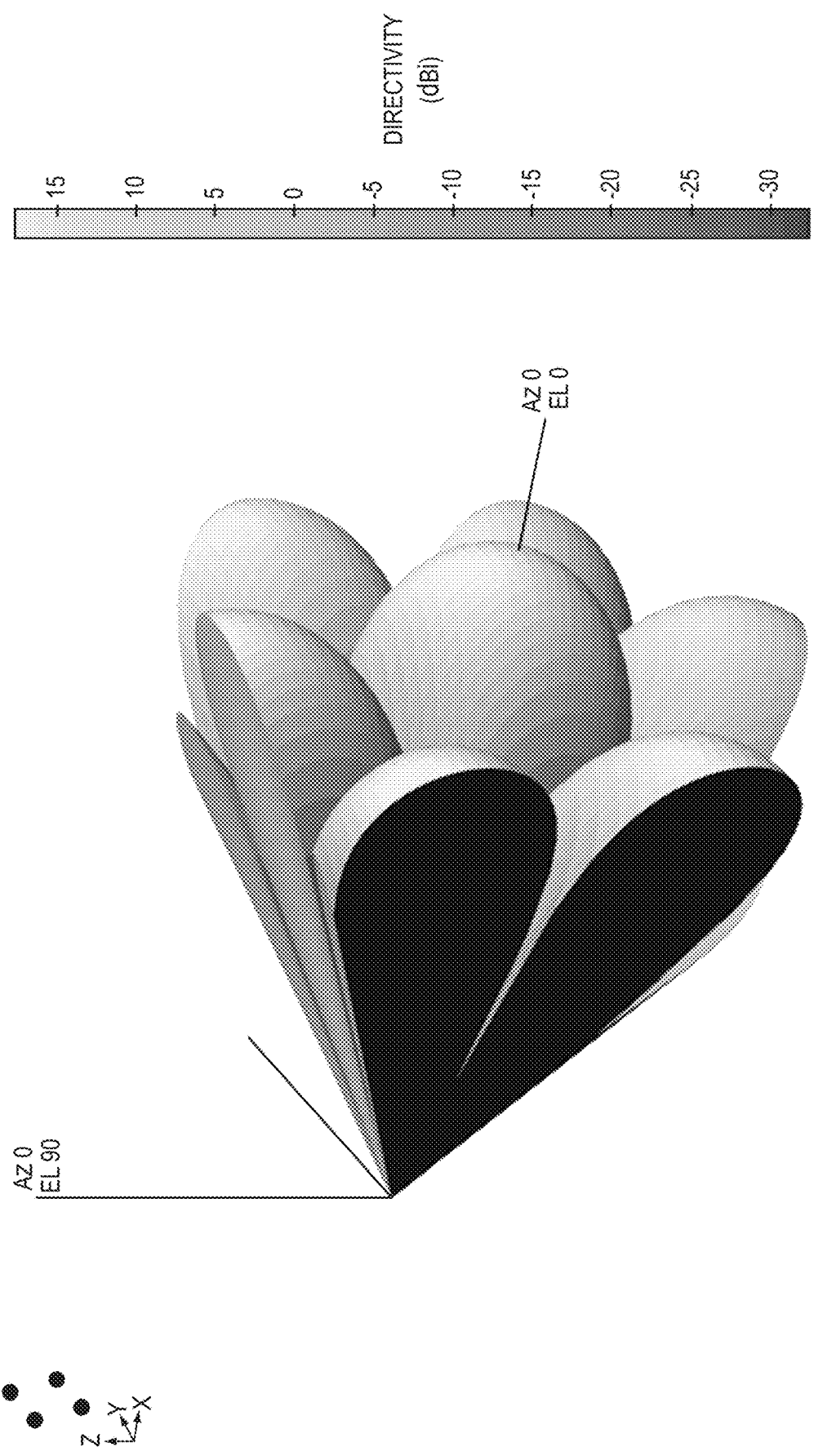
FIG. 13B illustrates a three-dimensional plot for the ½ beam width for a UTD configured in accordance with an embodiment of the present disclosure.

The broadband UTD variously disclosed herein provides numerous advantages over other approaches to DUs, such as ETU transducer devices discussed above. For example, a broadband UTD configured in accordance with the present disclosure advantageously utilizes multiple, single-frequency piezo plate arrays, which may be referred to herein as piezo sub-arrays plates. Each of the piezo elements of the piezo sub-array plates may output a ½ beam angle radiation pattern of about ±30 degrees or more. One such example ½ beam angle radiation pattern is shown in FIGS. 13A and 13B. Collectively, the piezo sub-array plates may output a beam angle radiation pattern to about 90 degrees. Thus, a fewer number of broadband UTD devices may be deployed to protect a given area relative to other approaches that have a relatively narrow beam angle radiation pattern. Environmental protections may be built in using, for instance, enclosed-type piezo electric transducer elements, which may further simplify design and reduce costs per unit while extending mean time between failure (MTBF) for each unit. In addition, piezo electric transducer elements may utilize a lower operating voltage than other approaches, e.g., ETU transducer devices, which allows for usage of relatively simpler and inexpensive driver circuitry and components.

Example Broadband Ultrasonic Transducer Device (UTD) and Operation

Figure 1:
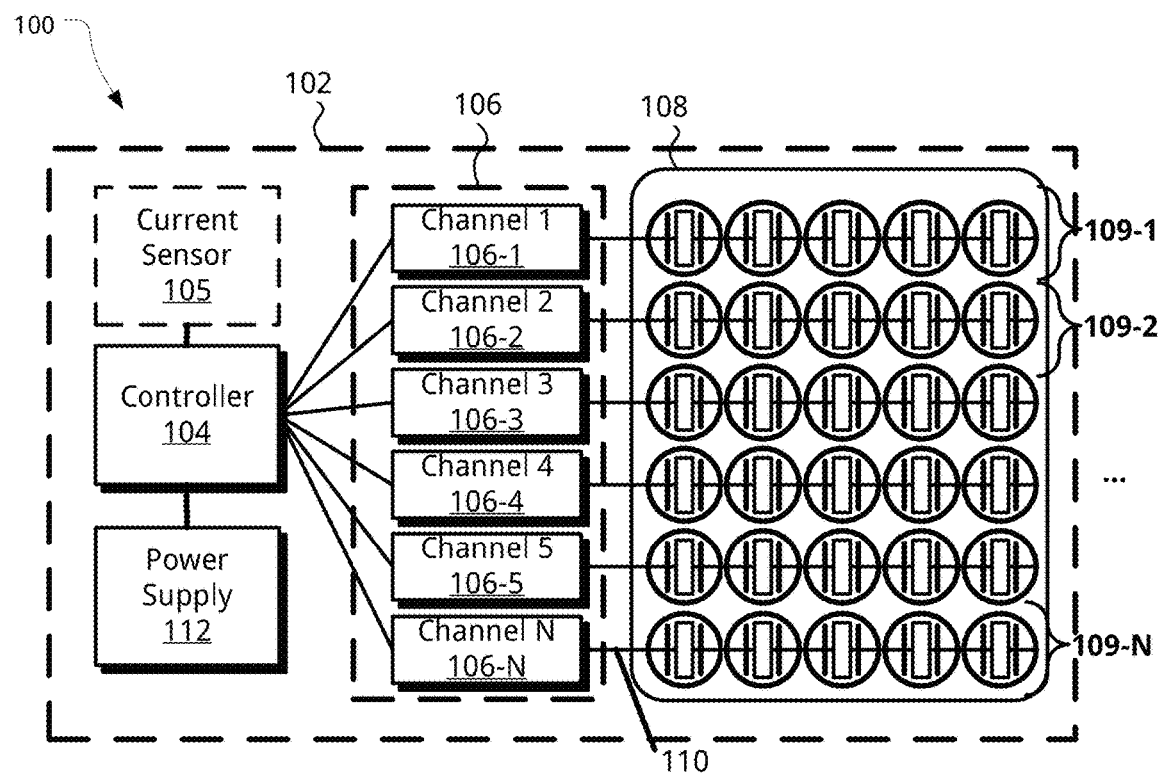
FIG. 1 shows a schematic view of an example broadband ultrasonic transducer device (UTD) configured in accordance with an embodiment of the present disclosure.

FIG. 1 shows an example broadband ultrasonic transducer device (UTD) 100 in accordance with an embodiment of the present disclosure. The broadband UTD 100 is shown in a highly simplified form and other embodiments are also within the scope of this disclosure. As shown, the broadband UTD 100 includes a housing 102. The housing 102 includes a controller 104, a plurality of channels collectively shown as channel drivers 106 and individually shown as channel drivers 106-1 . . . 106-N, an array of piezo electric transducers 108, and power supply circuitry 112.

Various scenarios and examples disclosed herein include the use of the broadband UTD 100 in outdoor environments or any other environment that requires consideration as to dust, heat, moisture and other conditions. The housing 102 may be ruggedized and sealed to prevent ingress of such contaminants. In some specific example cases, the housing 102 may comport with standards for ingress protection (IP) and have an IP67 rating for the housing 102 and associated cables and connectors (not shown) as defined within ANSI/IEC 60529 Ed. 2.1b, although other IPXY ratings are within the scope of this disclosure with the X denoting protection from solids and Y denoting protection from liquids. In some cases, the housing 102 comprises a plastic, polycarbonate, or any other suitably rigid material.

As discussed below, an embodiment of the housing 102 includes a multi-part housing including at least one removable portion, e.g., one or more cover portions, to allow for servicing of the broadband UTD 100. In this embodiment, the at least one removable portion couples to the housing 102 and forms a preventative seal, e.g. via an O-ring or other suitable device, to prevent ingress of contaminants such as water, dirt, and/or any other contaminating material present within a given operating environment. Some such example cover portions 504-1 to 504-6 are shown more clearly in FIG. 5.

While the example embodiment of FIG. 1 shows each component within the housing 102, this disclosure is not necessarily limited in this regard. For instance, the power supply circuitry 112 and controller 104 may not reside, e.g., be collocated, in the housing 102 along with the channel drivers 106 and the array of piezo electrical transducers 108. Numerous other alternatives and permutations are within the scope of this disclosure.

The controller 104 comprises at least one processing device/circuit such as, for example, a digital signal processor (DSP), a field-programmable gate array (FPGA), Reduced Instruction Set Computer (RISC) processor, x86 instruction set processor, microcontroller, or an application-specific integrated circuit (ASIC). Aspects of the controller 104 may be implemented using, for example, software (e.g., C or C++ executing on the controller/processor 104), hardware (e.g., hardcoded gate level logic or purpose-built silicon) or firmware (e.g., embedded routines executing on a microcontroller), or any combination thereof. In an embodiment, the controller 104 may be configured to carry out the processes 700, 900 and 1100, respectively.

The power supply circuitry 112 may be any suitable arrangement for supplying power to the broadband UTD 100. The power supply circuitry 112 may be configured to receive power from an external source (e.g., from AC main) and/or via one or more batteries (not shown). Although the power supply 112 is shown electrically coupled to the controller, the power supply 112 may couple to each of the channel drivers 106, for example, to provide power during operation of the broadband UTD 100.

Each of the channel drivers 106 may include amplification circuitry and piezo driver circuitry to drive associated piezo electric transducers of the array of transducers 108 based on a signal received from the controller 104, for example. Each of the piezo electric transducers of the array of transducers 108 may be implemented as enclosed-type transducers, which may be hermetically sealed. Enclosed-type transducers may be particularly advantageous for outdoor environments as they prevent against ingress of contaminants, and also for indoor environments characterized by dust and/or other contaminates. Each of the piezo electric transducers may include a metal housing with an integral metal diaphragm. A back of each piezo electric transducer may be completely sealed with a resin or other suitable sealant to protect from ingress of contaminants in a given environment. Other piezo electric transducer devices are within the scope of this disclosure, e.g., unenclosed types, and this disclosure should not be construed as limiting in this regard.

Figure 4:
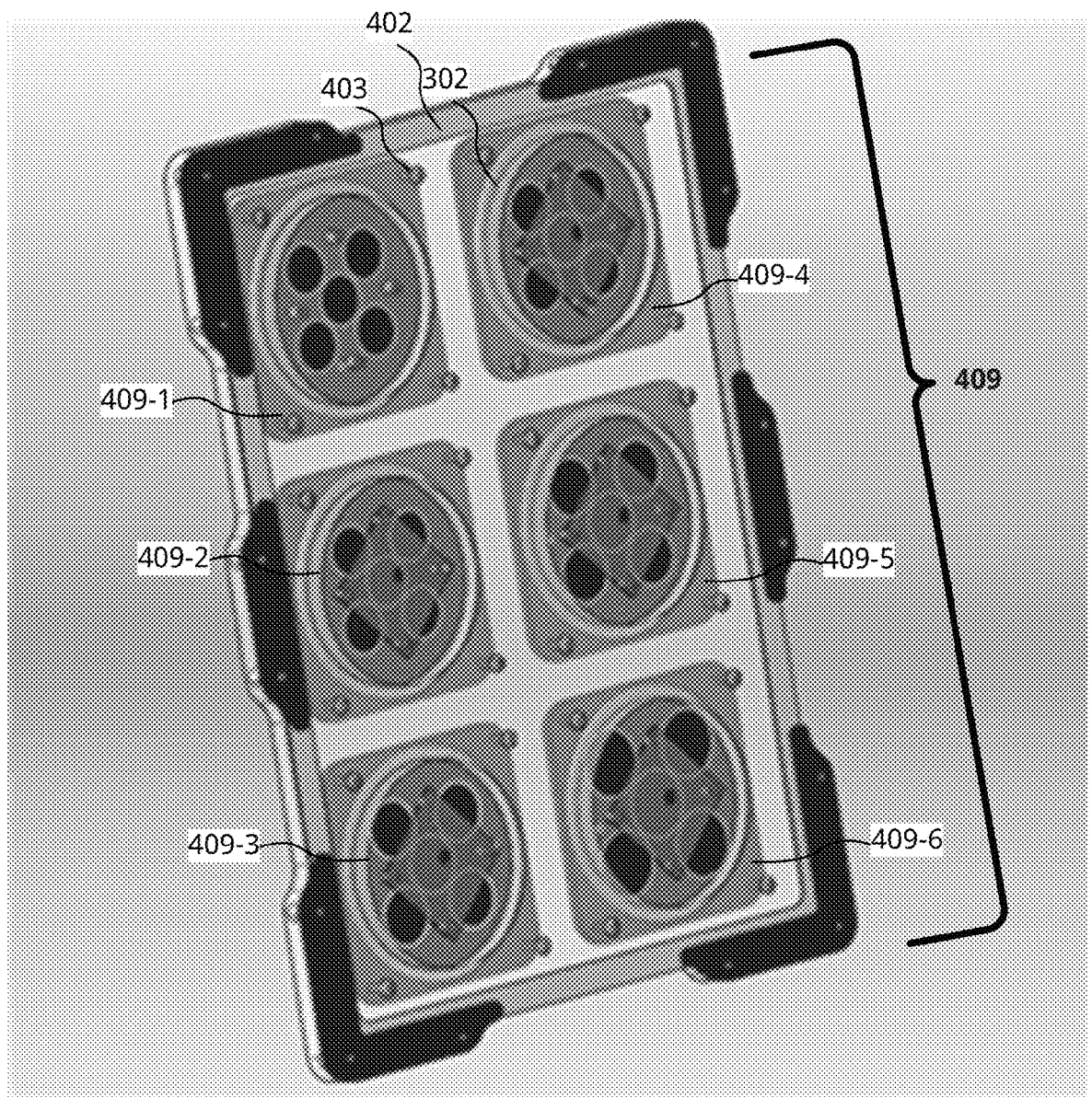
FIG. 4 shows an example perspective view of a broadband UTD housing with an array of piezo sub-array plates coupled thereto, in accordance with an embodiment of the present disclosure.

Each of the channel drivers 106-1 . . . 106-N is associated with a corresponding number of piezo electric transducer devices, which may also be referred to as piezo transducer elements. For clarity and practicality, each of the channel drivers 106-1 . . . 106-N is associated with a corresponding row of the array of transducers 108, with each row including N number of piezo electric transducers. In other embodiments, the array of transducers 108 is not necessarily patterned in linear rows and columns, e.g., as an M×N array. For example, as shown in FIG. 4, the array of transducers 108 are grouped into sub-array plates which are discussed in greater detail below.

Although five (5) piezo electric transducers are shown in each row of the array of transducers 108, this disclosure should not be limited in this regard. For example, each of the channel drivers 106-1 . . . 106-2 may be associated with 2, 5, 7, 10, or any number of piezo electric transducers depending on a desired configuration. In any event, each channel driver and associated piezo electric transducers may be collectively referred to as a "channel" or "output channel" herein. Thus, the channel driver 106-1 and associated piezo electric transducers 109-1 may be collectively referred to as Channel 1; channel driver 106-2 and associated piezo electric transducers 109-2 may be referred to as Channel 2, and so on.

Each piezo electric transducer of the array of transducers 108 may be configured substantially the same. For the sake of providing a specific non-limiting example, each of the piezo electric transducers of the array of transducers 108 may be implemented with a center frequency of 25 KHz±1 Khz, a minimum sound pressure level (SPL) of 113 dB, and a bandwidth of about 1.0 KHz. In other cases, different piezo electric transducer devices may be utilized. As discussed below, the physical characteristics of each piezo sub-array plate determine resonant frequency, and therefore, properties of the pocket/cavity coupled to each piezo electric transducer may be varied to achieve a nominal resonant frequency.

Each channel of the UTD 100 may thus be associated with an output frequency that is unique relative to the other channels based on the particular piezo transducer element used and the properties of the associated cavity/pocket which a piezo transducer element is coupled to. Each channel of the UTD 100 further includes a plurality of output resonant frequencies based on the bandwidth of a piezo electric transducer element. For example, each piezo electric transducer element may include a ±6 kHz bandwidth, although other bandwidths are within the scope of this disclosure. By way of example, consider Channel 1 having a nominal/design resonant frequency of about 25 KHz. In this example, the upper frequency and lower frequency values associated with this nominal frequency may include frequencies ranging from 28 kHz to 22 kHz, respectively. Channel 1 may therefore be driven to emit/output a resonant frequency in the range of 22 kHz to 28 kHz without endangering or otherwise degrading performance of the piezo electric transducers 109-1. Channel 2 may likewise be configured to be driven to emit/output a resonant frequency in the range of 29 kHz to 35 kHz based on a center frequency of 32 kHz, for example. Therefore, in accordance with an embodiment each channel of the broadband UTD 100 may be configured to cover an exclusive, non-overlapping range of resonant frequencies. In other cases, the broadband UTD 100 may be configured with channels having overlapping ranges or at least partially-overlapping ranges, e.g., that overlap by at least 1 kHz.

Figure 3A:
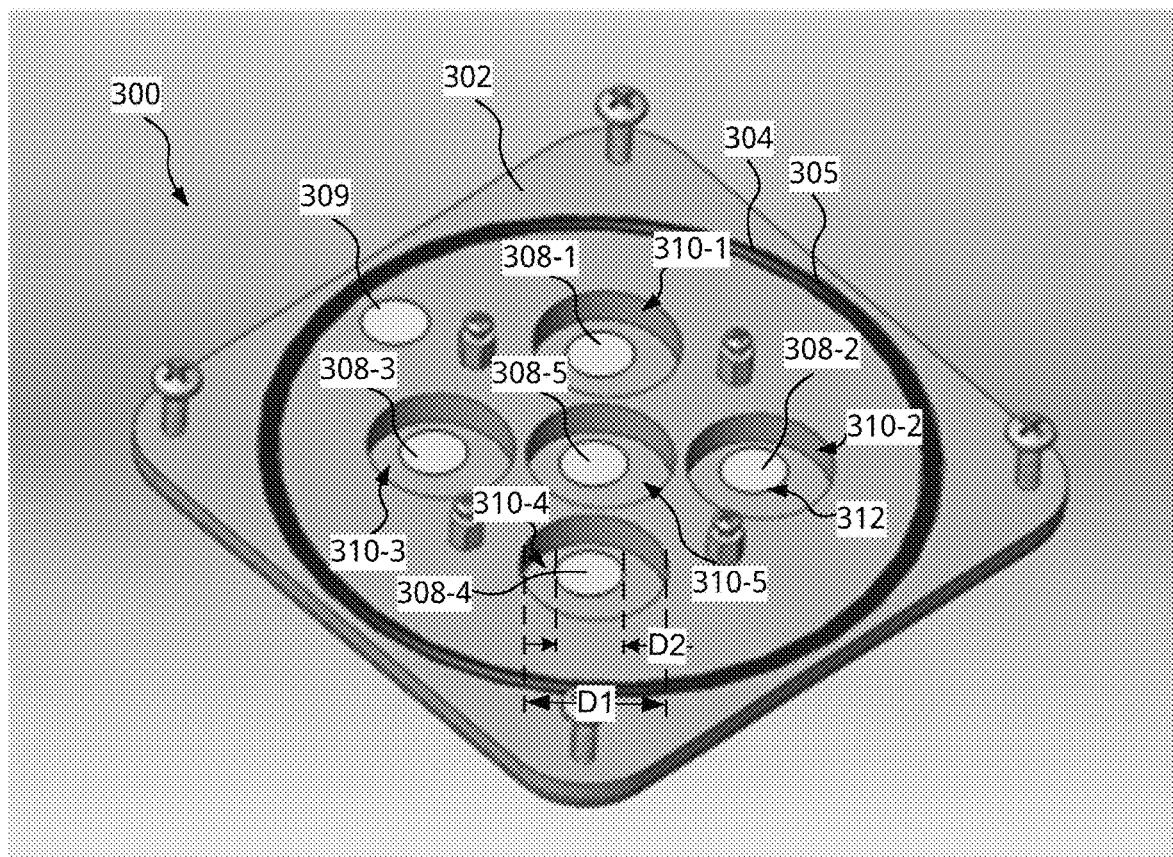
FIG. 3A shows an example piezo sub-array plate in accordance with an embodiment of the present disclosure.

In operation, the controller 104 provides a signal, e.g., a square wave, to each of the channel drivers 106 to cause an associated plurality of piezo electric transducers to emit at a particular resonant frequency. In turn, the channel drivers 106 may amplify the signal and provide the amplified signal to a respective plurality of piezo electric transducers of the array of piezo electric transducer devices 108. Each respective plurality of piezo electric transducers may be coupled to a piezo sub-array plate, which is discussed further below with reference to FIG. 3A.

The controller 104 may select a particular output frequency for a given channel by providing a signal to associated channel driver circuitry with a proportional frequency. A duty cycle of the signal provides the "on time" versus the "off time", which is to say the period of time when piezo electric transducers emit a particular output frequency versus the period of time when piezo electric transducers are off (or de-energized). Channel on time may be governed by a dwell time parameter. The overall ratio of on time to off time may be roughly equal, e.g., to provide a 50% duty cycle, although other duty cycles are also within the scope of this disclosure.

Continuing on, the controller 104 may cause one or more channels to emit a respective frequency simultaneously, with the maximum number of simultaneously emitted frequencies being equal to the total number of channels. For example, in a six (6) channel arrangement, such as shown in FIG. 1, the controller 104 may cause each of Channels 1 . . . 6 to emit six different frequencies simultaneously. To achieve a particular desired waveform, e.g., such as a white noise or colored noise waveform, the controller 104 may selectively drive one or more channels "on" while leaving others off in a random pattern. One specific example of colored noise generation by the broadband UTD 100 is discussed further below.

Figure 2:
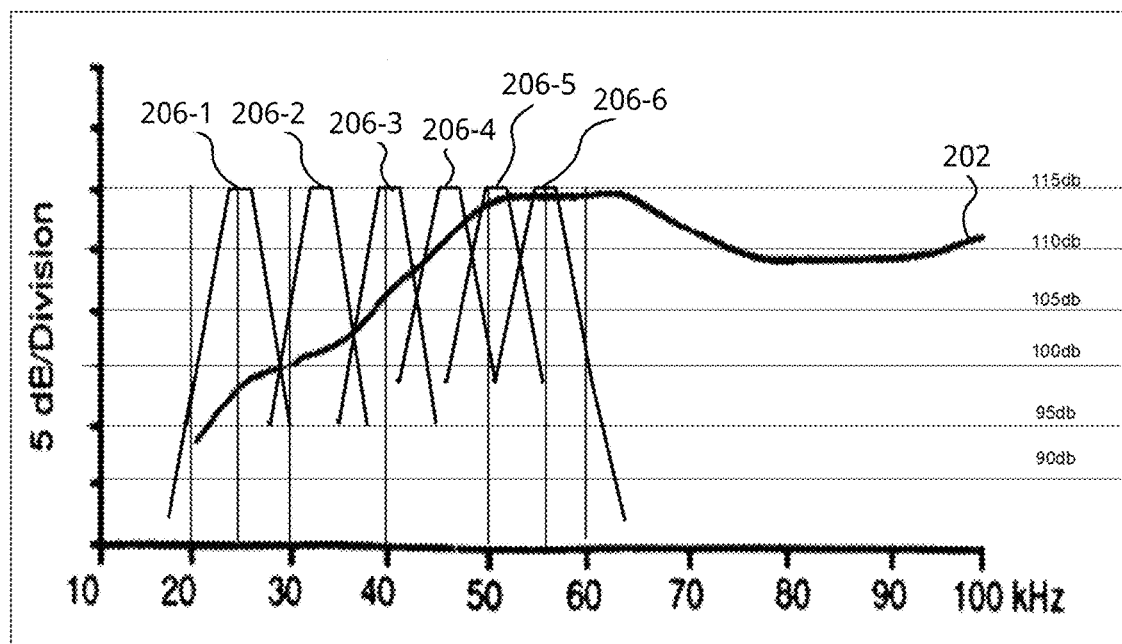
FIG. 2 shows a graph illustrating the sound pressure level (SPL) vs. frequency plot of an electro-static transducer with the frequency range of six (6) narrow band piezo electric transducers superimposed.

Turning to FIG. 2, a graph illustrates the SPL vs. frequency plot of an electro-static transducer 202 is shown and includes six (6) narrow band piezo electric transducers, e.g., piezo electric transducers 206-1 . . . 206-6, superimposed for purpose of contrast and comparison. As shown, the piezo electric transducer devices 206-1 . . . 206-6 create a relatively large SPL until about 48 kHz. This disclosure has identified that an array of narrow-band piezo electric transducers, e.g., the array of piezo electric transducers 108, may sufficiently approximate white noise, with white noise being defined as a generally random signal with a substantially constant power spectral density that has a finite bandwidth. In addition, the array of piezo electric transducers 108 may emit a single frequency to emit ultrasonic energy at a maximum SPL over a given period of time. The process 700 and 900 of FIGS. 7 and 9, respectively, provide some non-limiting example processes to achieve a desired SPL and output pattern for emitted ultrasonic energy.

Turning to FIG. 3, an example piezo sub-array plate 300 is shown that is suitable for use within the broadband UTD 100 of FIG. 1, in accordance with an embodiment of the present disclosure. The broadband UTD 100 may include N number of piezo sub-array plates, with each piezo sub-array plate being associated with a respective channel driver, e.g., channel drivers 106-1 . . . 106-N. Thus, the broadband UTD 100 may include a plurality of piezo sub-array plates to provide the array of piezo electric transducer devices 108, which is shown more clearly in FIG. 4.

Continuing with FIG. 3, the example piezo sub-array plate 300 includes a base 302 or base portion 302 that may be comprised from, for example, aluminum or other suitable material. The plate 302 or base portion 302 includes a plurality of openings, e.g., opening 310-1 . . . 310-5. Each opening 310-1 . . . 310-5 may be configured to receive a respective piezo electric transducer device. The openings 301-1 . . . 310-5 may be also be referred to as cavities or pockets. The openings 310-1 . . . 310-5 may be formed via milling or other suitable approach. Accordingly, each opening 310-1 . . . 310-5 may include a first diameter D1 that is larger than a diameter of an associated piezo electric transducer. Each opening 310-1 . . . 310-5 may further include at least an upper portion or cavity having the diameter D1 and a secondary/lower portion with a second diameter D2. The second diameter D2 may be configured substantially equal to that of the diameter of a respective piezo electric transducer. As shown, each of the piezo electric transducers 308-1 . . . 308-5 are disposed in a respective pocket of an associated opening 310-1 . . . 310-5, with a top surface of each piezo electric transducer being visible. In some cases, each of the piezo electric transducers 308-1 . . . 308-5 are glued into their respective pockets using an adhesive, for example.

The example piezo sub-array plate 300 may include an optional self-test piezo transducer device 309 to perform self-test processes. Each piezo sub-array plate may have an associated piezo transducer for providing feedback on the health of the drivers. Periodically piezo sub-array plates will be driven and the vibration energy will then be measured by the self-test piezo transducer device 309. The controller 104 may receive the measurement and then perform a fast Fourier transform (FFT) to calculate the magnitude and frequency of the vibration picked up by the self-test piezo transducer device 309. Pass/fail criteria may be set up, and if a failure occurs, e.g., a value exceeds a particular threshold, the UTD 100 may send out a warning signal, e.g., an audible beep or signal to a remote computer station, that a problem exists.

The example piezo sub-array plate 300 includes a groove 304 that surrounds the openings 310-1 . . . 310-5. An O-ring 305 may be disposed in the groove 304, such as shown, to provide a protective seal when a cover portion is coupled to the example piezo plate 300, which is shown more clearly in FIG. 5.

Figure 3B:
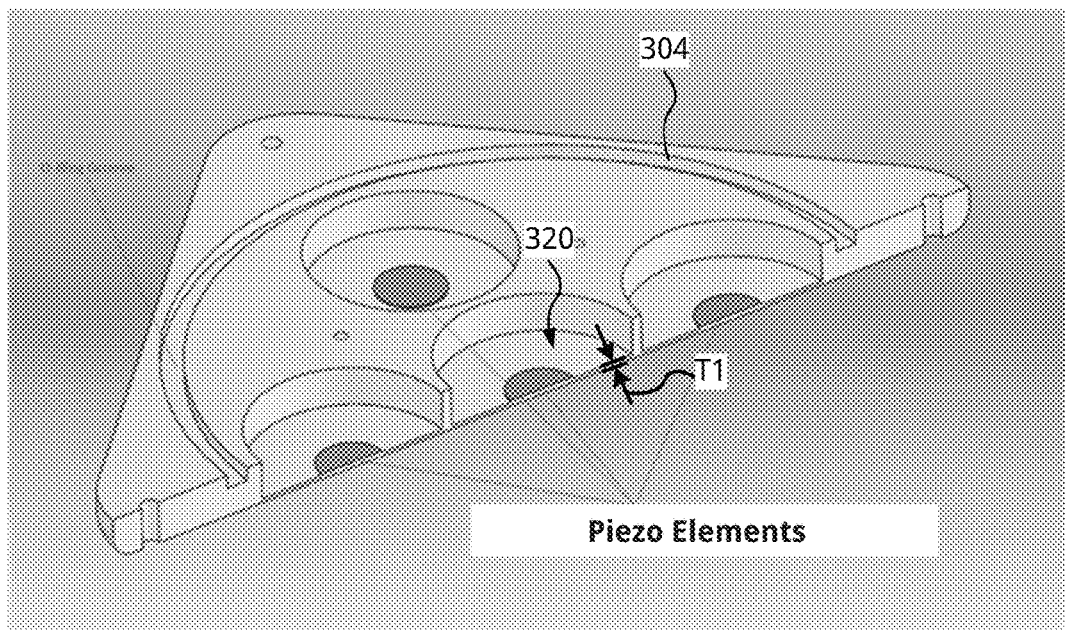
FIG. 3B shows a cross-sectional view of the piezo sub-array plate of FIG. 1 in accordance with an embodiment of the present disclosure.

Turning to FIG. 3B, with additional reference to FIB. 3A, a cross-sectional view of the example piezo sub-array plate 300 is shown in accordance with an embodiment of the present disclosure. Each piezo sub-array plate 300 may be specifically designed to emit a particular resonant frequency based on physical and material features such as diameter of an associated opening, e.g., diameter D1, the thickness of the material adjacent each piezo electric transducer, e.g., thickness T1 of metal face 320 or metal bending element 320, and Young's Modulus of the material of the material adjacent each piezo electric transducer. The material immediately adjacent each piezo electric transducer, which is to say the metal bending element 320, may be formed from other materials and is not necessarily limited to a metal or metal alloy. Thus, the resonant frequency for each piezo sub-array plate may be calculated based on the following equations:

$$RFreq = \alpha\left(\frac{h}{rdisk^2}\right) \quad \text{Equation (1)}$$

$$\alpha = 0.412\left(\sqrt{\left(\frac{Y}{0.91\rho}\right)}\right) \quad \text{Equation (2)}$$

where RFreq is the resonant frequency (in kHz) after a piezo electric transducer element is glued/coupled into a respective opening, α is an approximation (e.g., Poisson's ratio) of the compressibility of the material of the bending element, h is the thickness of the bending element, Y is Young's Modulus, p is the density of ceramic material, and rdisk is the radius of the bending element. Thus, each piezo electric transducer subarray includes a plurality of openings with diameters and material thicknesses to provide a particular desired resonant frequency. Each plate may be configured with substantially different sized openings, and more particularly opening diameters and material thicknesses to provide an associated resonant frequency when driven.

As sound travels through the air, the magnitude of the sound pressure is reduced due to both absorption (attenuation) and spreading loss caused by the expanding surface of the radiating beam as the sound pulse travels from the transducer. The SPL at a distance R from the transducer is given by:

$$SPL(R)=SPL(R_0)-20 \log(R/R_0)-\alpha(f)R \quad \text{Equation (3)}$$

where SPL(R) is the sound pressure level at distance R in dB//1 μPa, SPL(R0) is the sound pressure level at distance R0 in dB//1 μPa, and α(f) is the attenuation coefficient in dB/unit distance at frequency f.

The ½ beam width for a single piezo electric transducer is given by the equation:

$$\frac{\sin\alpha}{2} \cong Vair/D\theta f \quad \text{Equation (4)}$$

Where α is the angular width of the main beam, f is the frequency, Dθ is the diameter of area radiating, and Vair is the velocity of sound in air (e.g., ~344 meters/second).

As the sound travels, the amplitude of the sound pressure is reduced due to friction losses in the transmission medium. Knowing the value of this absorption loss, or attenuation, is important in determining the range of each piezo sub-array plate. The attenuation of sound in air increases with the frequency (e.g., based on Stokes law of sound attenuation), and at any given frequency the attenuation varies as a function of humidity. The value of humidity that produces the maximum attenuation is not the same for all frequencies. Above 125 kHz, for example, the maximum attenuation occurs at 100% RH; at 40 kHz, maximum attenuation occurs at 50% RH.

One estimate for the maximum attenuation in air at room temperature over all humidity's for frequencies up to 50 kHz is given by:

$$\alpha(f)=0.01f \qquad \text{Equation (5)}$$

where $\alpha(f)$ is maximum attenuation in dB/ft, and f is the frequency of sound in kHz.

Therefore, between 50 kHz and 300 kHz, for example, the maximum attenuation over all humidity's is:

$$\alpha(f)=0.022f-0.6 \qquad \text{Equation (5)}$$

Turning to FIG. 4, a perspective view shows a plurality of piezo sub-array plates 409 coupled to a housing portion 402, in accordance with an embodiment of the present disclosure. As shown, the housing portion 402 includes a plurality of piezo sub-array plates collectively shown at 409, and individually shown as piezo sub-array plates 409-1 . . . 409-6 mounted thereon. The housing portion 402 may be formed from, for example, Plexiglas or any other suitable materials such as a plastic or polycarbonate. Each of the piezo sub-array plates 409-1 . . . 409-6 couples to the housing portion 402 via a fastening member such as one or more screws 403. Each of the piezo sub-array plates 409-1 . . . 409-6 may be acoustically (e.g., vibrations from adjacent piezo sub-array plates have negligible or otherwise no effect) and electrically isolated from each other. The piezo sub-array plates 409-1 . . . 409-6 may be arranged in an M×N array, such as shown. As previously discussed, each of the piezo sub-array plates 409-1 . . . 409-6 include associated piezo electric transducers having an identical or substantially similar nominal frequency. Piezo sub-array plate 409-1 may be associated with Channel 1, e.g., be electrically coupled to channel driver 106-1, piezo sub-array plate 409-2 may be associated with Channel 2, e.g., be electrically coupled to channel driver 106-2, and so on.

Figure 5:
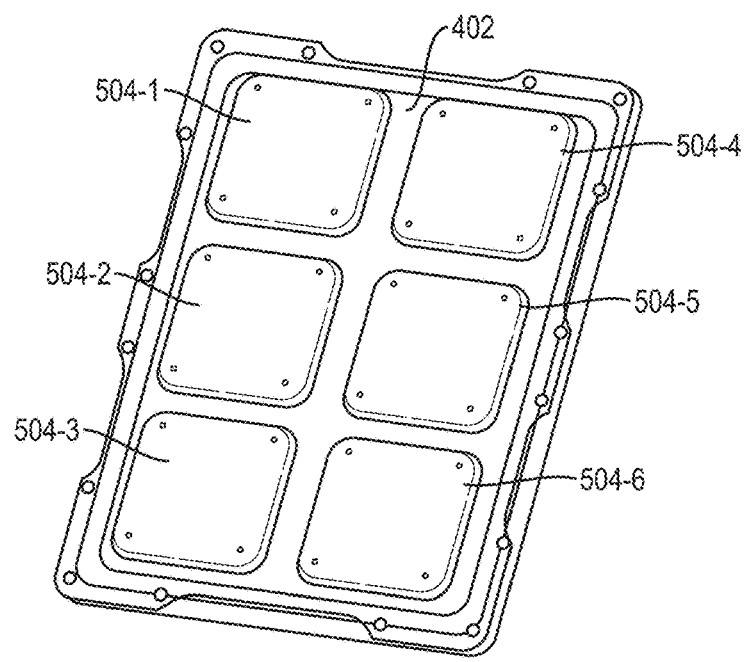
FIG. 5 shows another example perspective view of the broadband UTD housing of FIG. 4 with cover portions coupled to each respective piezo sub-array plate, in accordance with an embodiment of the present disclosure.
Figure 6:
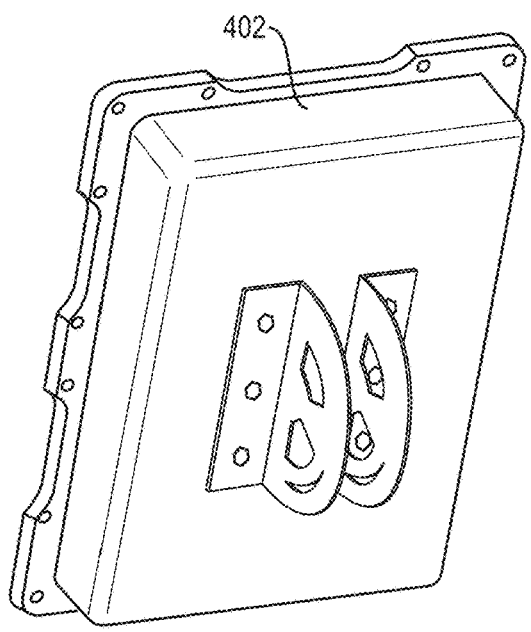
FIG. 6 shows another example perspective view of a back side of the broadband UTD housing of FIG. 4, in accordance with an embodiment of the present disclosure.

Turning to FIG. 5, a prospective view of the housing portion 402 is shown in accordance with an embodiment of the present disclosure. As shown, the housing portion 402 includes a plurality of cover portions 504-1 . . . 504-6 coupled to respective ones of piezo electric sub-array plates 409-1 . . . 409-6 (FIG. 4). Each of the cover portions 504-1 . . . 504-6 may form a seal, e.g., based on an O-ring in groove 304, with each respective piezo sub-array plate. FIG. 6 shows a back perspective view of the housing portion 402.

Figure 14:
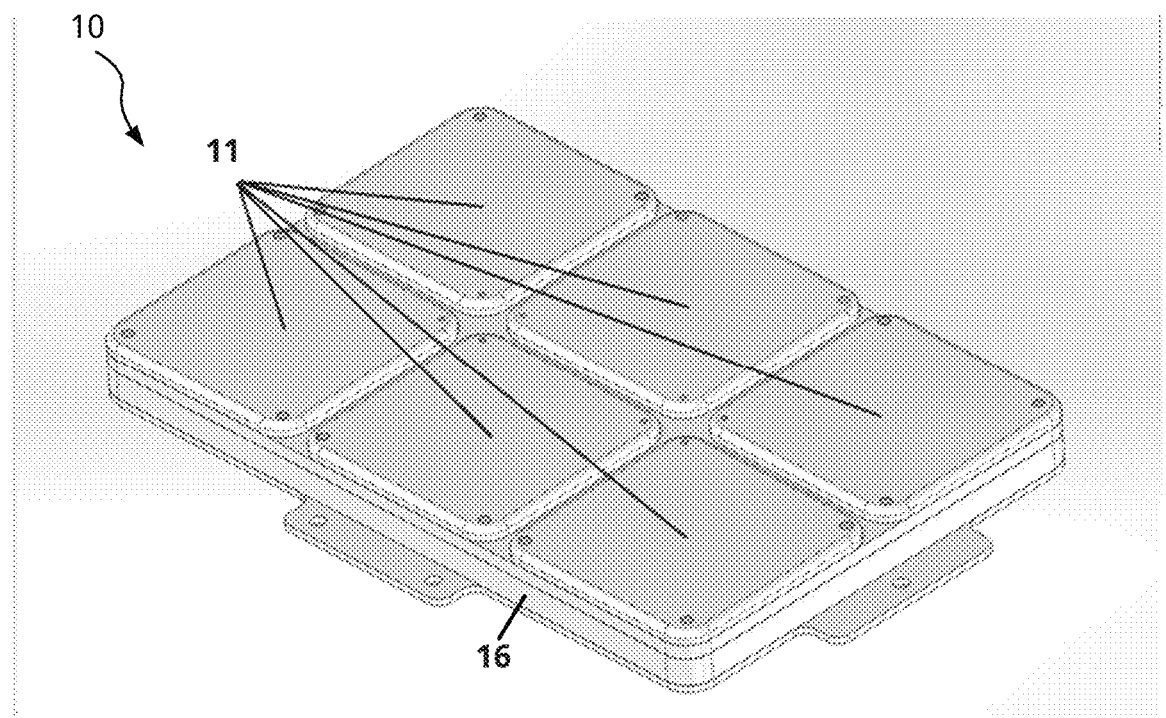
FIG. 14 shows an example perspective view of a broadband UTD in accordance with an embodiment of the present disclosure.

Turning to FIG. 14, another example embodiment of a broadband UDT 10 is shown. The broadband UDT 10 may be configured substantially similar to that of the broadband UDT discussed above with reference to FIGS. 1-6, the description of which will not be repeated for brevity. As shown, the broadband UDT 100 includes an elongated rectangular housing 16 having a plurality of piezo sub-arrays, e.g., piezo sub-array 300A shown more clearly in FIG. 16, and a corresponding plurality of sub-array cover portions 11. The housing 16 may comprise, for example, a metal such as aluminum or any other suitably rigid material.

Figure 15:
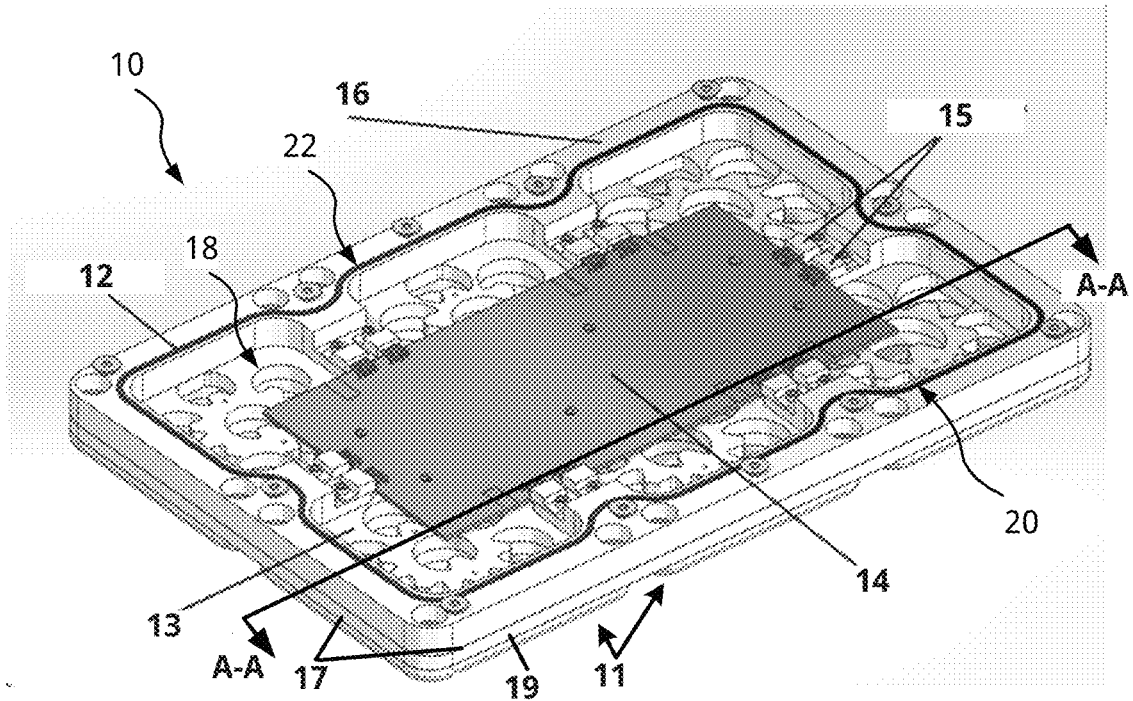
FIG. 15 shows another example perspective view of the broadband UTD of FIG. 14 in accordance with an embodiment of the present disclosure.

Turning to FIG. 15, a bottom perspective view the broadband UDT 10 is shown in accordance with an embodiment of the present disclosure. As shown, the housing 16 includes a plurality of sidewalls, e.g., sidewalls 17, that extend from the housing portion 19. The housing portion 19 couples to the array of piezo sub-array plates, e.g., piezo sub-array plate 300A. The housing portion 19 may include a plate 13 formed from a polycarbonate material or other suitably rigid, non-conductive material. The plate 13 may include a plurality of openings, which are more clearly shown in FIG. 16. The housing 16 may further include a channel 22 to receive a gasket 12, with the channel 22 extending continuously around a perimeter of the housing 16. The gasket 12 may form a protective seal to prevent ingress of contaminants when a corresponding removable cover portion (not shown) is coupled to the housing 16.

The housing 16 further defines a cavity 18. The cavity may include a substrate 14. The substrate 14 may couple to the plate 13. The substrate 14 may comprise a circuit board, for example, or other suitable substrate material for mounting of electrical components. The substrate 14 includes a plurality of connectors 15, with each connector electrically coupling an associated piezo sub-array disk to circuitry of the substrate 14. In an embodiment, the substrate 14 includes the controller 104, power supply circuitry 112, and the channel driver circuitry 106-1 . . . 106-N. The plurality of connectors 15 may therefore connect each piezo sub-array plate to associated channel driver circuitry.

Figure 16:
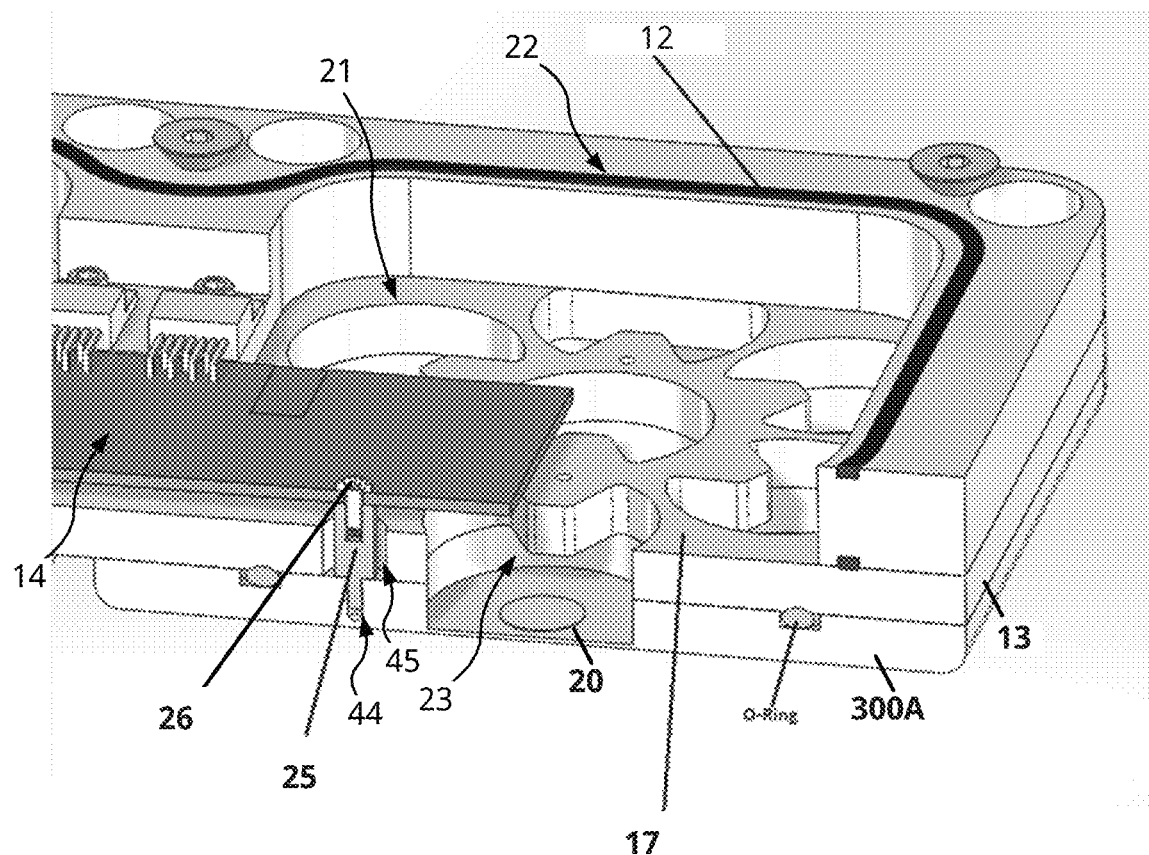
FIG. 16 shows a cross-sectional view of the broadband UTD of FIG. 15 taken along line A-A, in accordance with an embodiment of the present disclosure.
Figure 19:
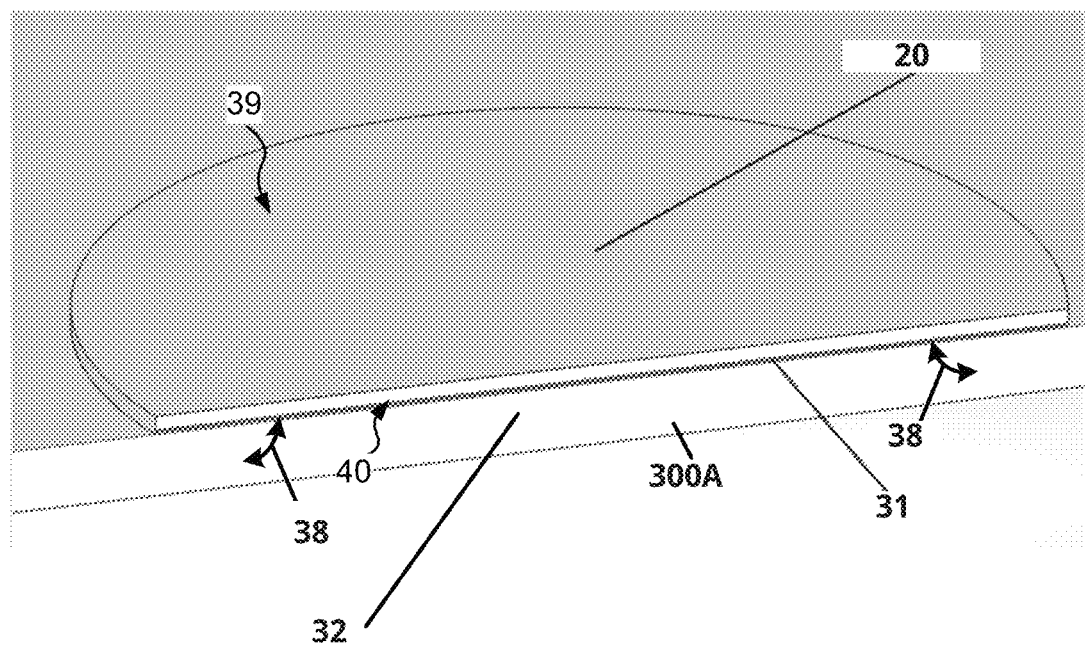
FIG. 19 shows an example cross-sectional view of a piezo element coupled to a piezo sub-array plate via a conductive adhesive, in accordance with an embodiment of the present disclosure.

FIG. 16, with additional reference to FIG. 19, shows of cross-sectional view of the broadband UDT 10 of FIGS. 14 and 15, in accordance with an embodiment of the present disclosure. As shown, the plate 13 includes a plurality of openings 21 that correspond with openings in each piezo sub-array plate, e.g., opening 23, that contain piezo elements, e.g., piezo element 20. Piezo sub-array plate 300A may be configured substantially similar to that of piezo sub-array plate 300 of FIG. 3, the description of which will not be repeated for brevity. As further shown, the piezo sub-array plate 300A may provide a conductive path by virtue of the material forming the same, with the conductive path 38 being more clearly shown in FIG. 19. For example, the piezo sub-array plate 300A may comprise a metal, e.g., such as aluminum, or other electrically conductive material.

A bottom surface 40 of each piezo element 20 may provide a negative terminal. Therefore, the conductive path 38 may be utilized to provide a negative return path between the piezo element 20 and associated circuitry of the substrate 14, for example. A top surface 39 of each piezo element 20 may provide a positive terminal, which may be coupled to associated driver circuitry via a stretchable conductive fabric material 41, which is discussed further below with reference to FIG. 17. An interconnect device 25 may provide electrical conductivity by having a first portion that electrically couples to the substrate 14 and a second portion that electrically couples to the piezo sub-array plate 300A. In some cases, such as shown, the interconnection device 25 directly contacts a portion of the sub-array plate 300A and also directly contacts a portion of the substrate 14, e.g., an electrical pad. The piezo sub-array plate 300A may include an opening 44 to receive at least a portion of each interconnect device 25. Each opening 44 may correspond with an opening 45 of the plate 13 to allow the interconnect device 25 to pass through the plate 13 into the opening 44.

A screw 26 or other suitable fastening member may electrically couple the substrate 14 to the interconnect device 25, and may also mechanically mount the substrate 14 securely within the broadband UDT 10. To this end, circuitry of the substrate 14, e.g., channel driver circuitry, may electrically couple to an associated piezo sub-array plate in a direct manner without an intermediate device, e.g., a flexible printed circuit (FPC) board, that must be routed/bent within the UDT 10 or soldering that may degrade over time due to mechanical vibrations, for example.

Figure 17:
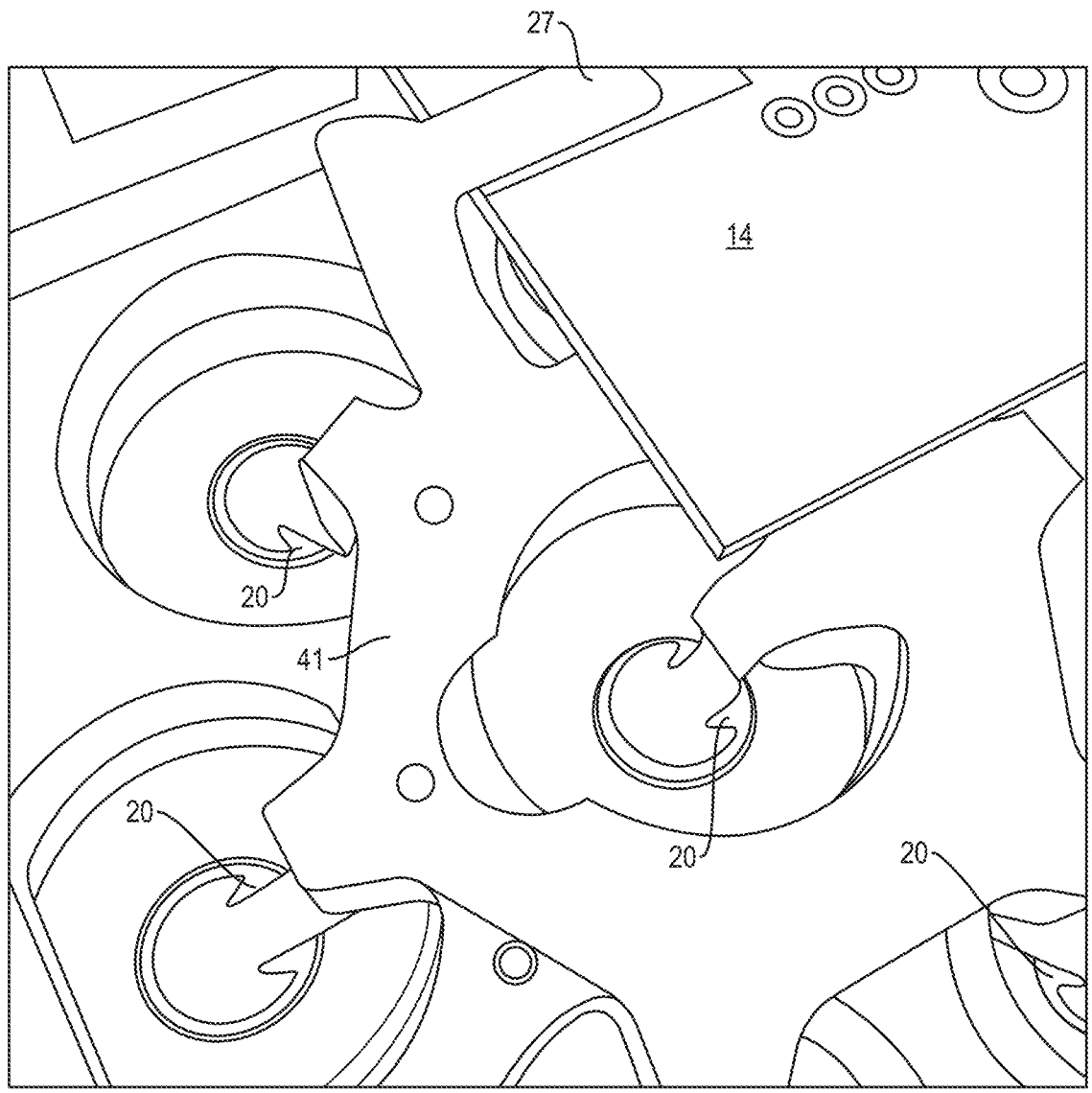
FIG. 17 shows a flexible conductive material electrically coupling piezo elements to associated circuitry of a broadband UTD, in accordance with an embodiment of the present disclosure.

Turning to FIG. 17, a view of the broadband UDT 10 is shown in accordance with an embodiment of the present disclosure. As shown, a flexible conductive material 41 electrically couples each of the piezo elements 20, e.g., via an electrical terminal provided by a surface of each piezo element 20 as discussed above, to associated circuitry of the substrate 14, e.g., via electrical pad/terminal 27. The flexible conductive material 41 may comprise, for example, a silver-coated stretchable material. The flexible conductive material 41 may comprise other configurations, e.g. a different metal or conductive material, and is not necessarily limited to a silver coating. The flexible conductive material 41 may be coupled to each of the piezo elements via, for example, an adhesive or other suitable approach.

Figure 18:
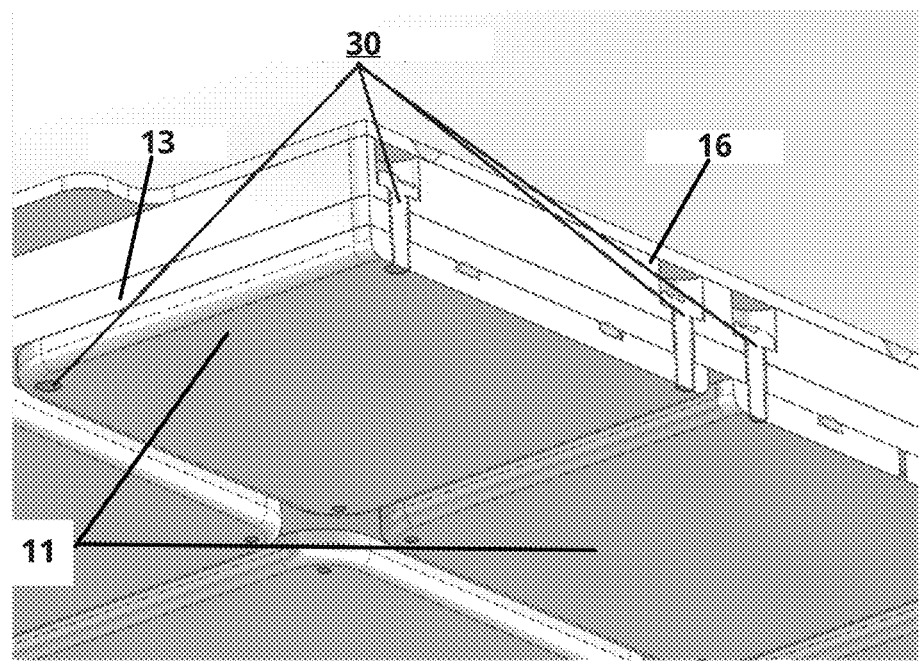
FIG. 18 shows another cross-sectional view of the UTD of FIG. 14 in accordance with an embodiment of the present disclosure.

Turning to FIG. 18, a cross-sectional view of the broadband UTD of FIG. 14 is shown in accordance with an embodiment of the present disclosure. As shown, non-conductive fastening members 30 couple each piezo sub-array plate, e.g., piezo sub-array plate 300A, and corresponding cover portion 11 to plate 13 and the housing portion 16. The non-conductive fastening member 30 may comprise, for example, a plastic screw. To this end, each piezo electric sub-array plate may be electrically isolated from the housing portion 16.

FIG. 19 shows a cross-sectional view of the piezo element 20 of FIG. 16 in accordance with an embodiment of the present disclosure. As shown, an adhesive layer 31 is disposed between the piezo element 20 and the bending element 32. The adhesive layer 31 may comprise, for example, an epoxy bond mixed with nickel spheres, with the nickel spheres being 3%-5% by weight, although other concentrations are within the scope of this disclosure. The adhesive layer 31 may advantageously provide electrical conductivity between the piezo element 20 and a surface of the bending element 32. However, other conductive adhesive materials may be utilized and the provided examples are not intended to be limiting to the present disclosure.

Example Methodologies and Architecture

A broadband UTD in accordance with the present disclosure, e.g., the broadband UTD 100, advantageously utilizes a plurality of narrow-band piezo electric transducer subarrays to provide a broad-range of selectable output frequencies. In addition, a broadband UTD in accordance with the present disclosure provides significant advantages over other approaches as the broadband UTD includes a relatively simple mechanical design that provides protection from environmental factors such as dust, moisture and other contaminates. One specific example application particularly well suited for the broadband UTD variously disclosed herein includes wildlife deterrence. Wildlife deterrence applications require a device with a design that prevents the aforementioned contaminants from causing component failure and shortened life spans, e.g., mean time between failures (MTBFs).

Figure 7:
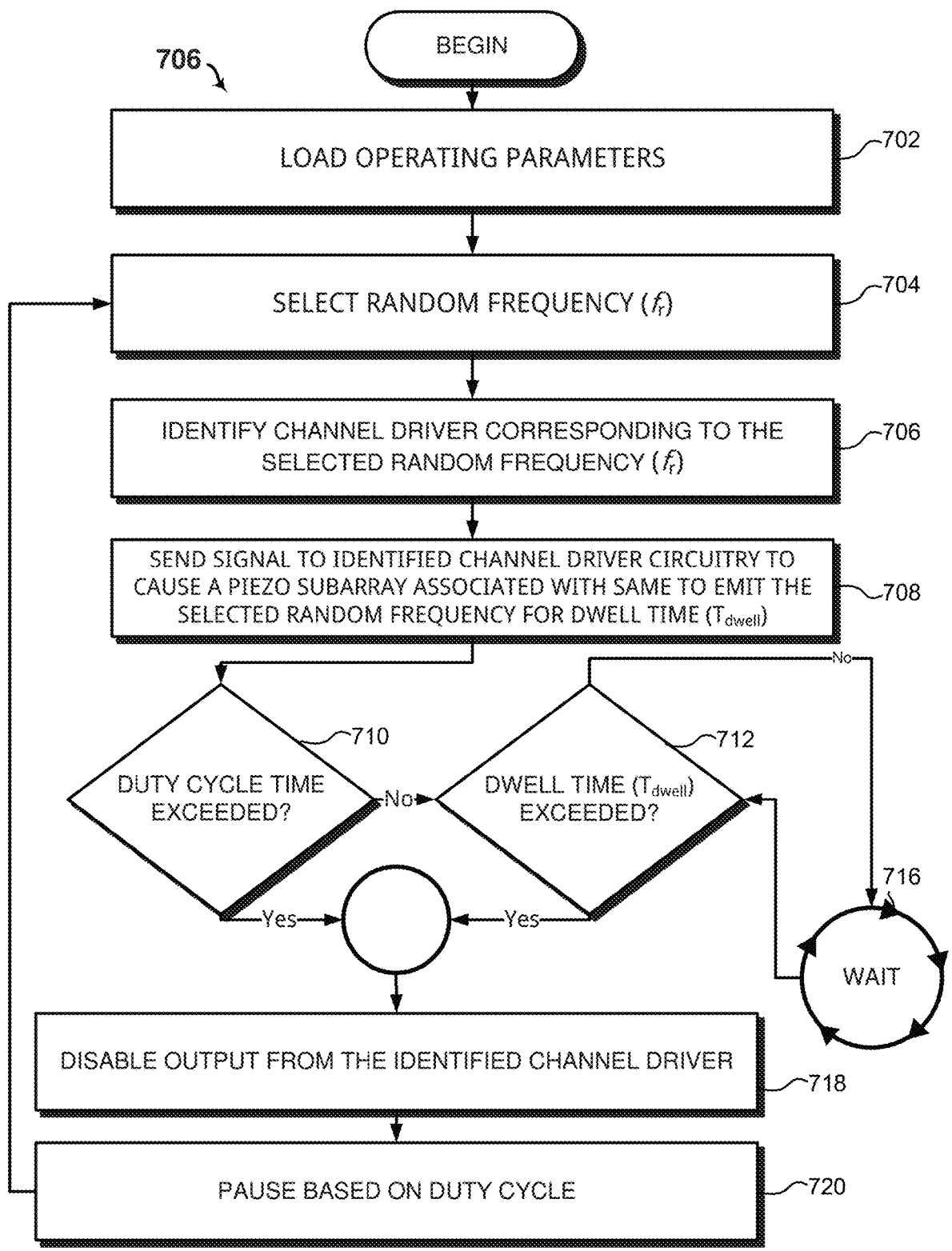
FIG. 7 shows an example process for driving a plurality of piezo sub-arrays to emit a random resonant frequency, in accordance with an embodiment of the present disclosure.

A wildlife deterrent process may be implemented in a variety of ways. FIG. 7 is a flow chart illustrating one deterrent unit (DU) process 700 useful in connection with a system and method consistent with the present disclosure. The DU process 700 may be performed whole, or in part, by the controller 104 or any other suitable controller of a broadband UTD configured in accordance with the present disclosure. While flowcharts presented herein illustrate various operations according to example embodiments, it is to be understood that not all of the depicted operations are necessary for other embodiments. Indeed, it is fully contemplated herein that in other embodiments of the present disclosure, the depicted operations, and/or other operations described herein, may be combined in a manner not specifically shown in any of the drawings, but still fully consistent with the present disclosure. Thus, claims directed to features and/or operations that are not exactly shown in one drawing are deemed within the scope and content of the present disclosure.

In act 702, the controller 104 loads operating parameters from a memory. Table 1 summarizes some example non-limiting parameters that may be loaded by the controller 104 for a six-channel configuration. While process 700 specifically references a broadband UTD with a 6-channel configuration, this disclosure is not necessarily limited in this regard and other channel configurations with more or less channels are within the scope of this disclosure.

TABLE 1

| Example Operating Parameters | | | | | | |
|---|---|---|---|---|---|---|
| Configuration Parameter | CH1 | CH2 | CH3 | CH4 | CH5 | CH6 |
| Nominal Frequency (kHz) | 25K | 32K | 40K | 47K | 51K | 57K |
| Upper Frequency (Hz) | 28K | 35K | 43K | 49K | 54K | 60K |
| Lower Frequency (Hz) | 22K | 29K | 37K | 44K | 50K | 55K |
| Dwell Time (s) | 0.01 | 0.01 | 0.01 | 0.01 | 0.01 | 0.01 |
| Duty Cycle | 50% | 50% | 50% | 50% | 50% | 50% |

The parameters provided in Table 1 correspond to nominal resonant frequencies for each of the piezo electric subarrays for a UTD device configured in accordance with the present disclosure. Stated differently, each piezo electric transducer subarray includes a plurality of piezo electric transducer elements and corresponding openings, with geometries and material properties associated therewith providing a nominal resonant frequency, as discussed above. Therefore, the resonant frequency for each channel, e.g., CH1 . . . CH6, is known and is represented by a value that may be stored in a memory associated with the controller 104, for example. Each channel may also be associated with other parameters such as the upper and lower frequencies (in kHz), dwell time (in milliseconds) and a duty cycle, for example.

In act 704, the controller 104 selects a random frequency value (fr), with the random frequency value being bounded between a minimum lower frequency value, e.g., 22 kHz, and a maximum upper frequency value, e.g., 60 kHz. For example, given the parameters outlined in Table 1, the minimum lower frequency is associated with Channel 1 at 22 kHz and the maximum upper frequency is associated with Channel 6 at 60 kHz. Therefore, the controller 104 selects a random number representing a frequency between 22 kHz and 60 kHz. The resolution of the random number representing the frequency is about 100 hz, or may be other values depending on a desired implementation.

In act 706, the controller 104 identifies a channel driver, e.g., one of channel drivers 106, that corresponds to the selected random frequency value (fr). This may include the controller 104 examining each upper and lower frequency to determine which channel corresponds with the selected random frequency value value (fr). For example, if the selected random number corresponds to a frequency of 52.2 kHz, then the controller 104 may compare the same with parameters in memory to identify the fifth channel as having a range of frequencies that can service the 52.2 kHz frequency (e.g., 50 kHz<52.2 kHz<54 kHz).

In act 708, the controller 104 sends a signal to the channel identified in act 706 to cause a piezo subarray associated with the same to emit the selected random frequency for a dwell time $T_{dwell}$. The dwell time may be based on the dwell time parameter associated with the channel identified in act 706. For example, and continuing the previous example, the controller 104 may provide a signal to the fifth channel, and more particularly, to the channel driver 106-5. In response, the channel driver 106-5 may cause an associated piezo subarray, e.g., piezo subarray 409-5, to emit the selected random frequency of 52.2 kHz for the dwell time $T_{dwell}$, which in this example case is 0.01 seconds. The channel driver 106-5 may amplify the signal from the controller 104 in this example or otherwise convert the signal into a proportional electrical signal for piezo driving purposes.

In act 710, if the overall amount of time the controller 104 has driven associated channels is greater than a defined duty cycle time, e.g., 50%, the process 700 continues to act 718. Otherwise, the process 700 continues to act 712. For example, for every 10 seconds of operation the controller 104 may turn channels "on" for 5 seconds and "off" for the other 5 seconds based on a duty cycle of 50%, although this example duty cycle should not be construed as limiting. The controller 104 may utilize a hardware and/or software timer to measure duty cycle.

In act 712, the controller 104 determines if the amount of time a particular channel is "on" exceeds an associated dwell time. For example, in the prior example the controller 104 provides a signal to the channel driver 106-5 to cause the same to drive an associated piezo subarray for 0.01 seconds (e.g., the dwell time $T_{dwell}$ associated with Channel 5) at 52.2 kHz. The controller 104 may initiate a timer to determine if the dwell time $T_{dwell}$ has elapsed. If the dwell time $T_{dwell}$ has been exceeded/elapsed, then the process 700 continues to act 718. Otherwise, the process continues to act 716. In act 716, the controller 104 waits for a predetermined amount of time, e.g., a few microseconds, before returning to act 712.

In act 718, the controller 104 disables output from channel driver identified in act 706 to prevent the same from continuing to emit the random frequency selected in act 708. In act 720, the controller 104 pauses for a period of time based on the duty cycle before returning to act 704 and selecting a new random frequency value. As discussed above, the controller 104 may seek to operate the channels at a 50% duty cycle. Therefore, the period of time chosen by the controller 104 to effectively turn "off" the channels may equal that of the total "on" time. For example, if the duty cycle time is 5 seconds then a corresponding off time will be roughly the same, assuming a duty cycle of 50%. Other duty cycles are within the scope of this disclosure and the provided examples are not intended to the limiting.

Figure 8:
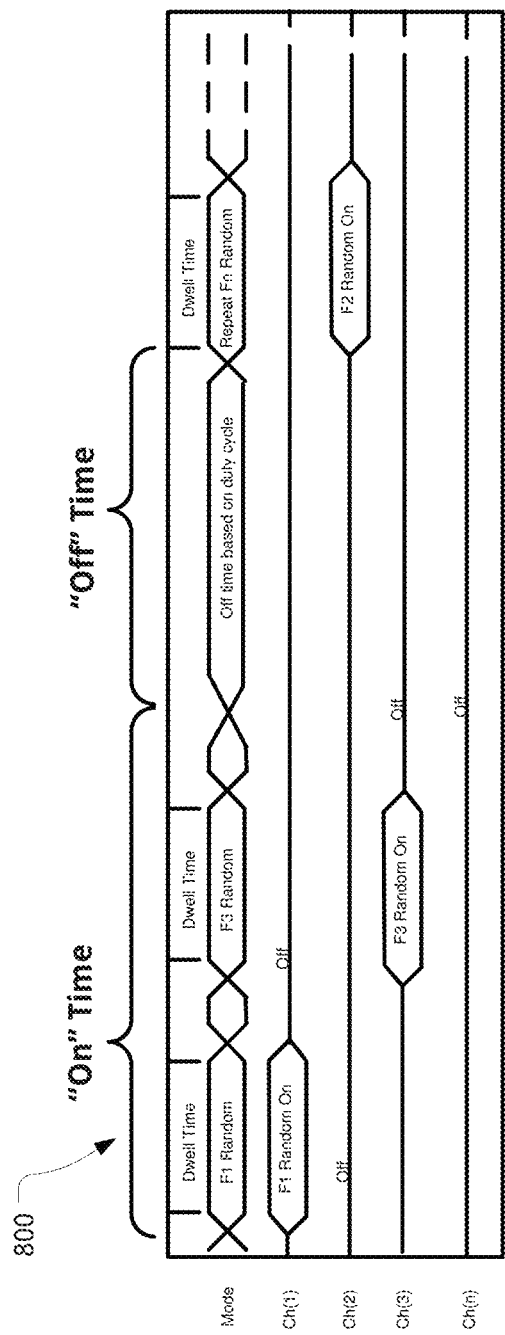
FIG. 8 shows an example timing diagram for a broadband UTD during performance of the example process of FIG. 7.

Turning to FIG. 8, an example timing diagram is shown in accordance with the controller 104 performing the process 700 of FIG. 7. As shown, during a first period of time labeled "On" time, the controller 104 selected a first random frequency (F1) corresponding to Channel 1. The controller 104 therefore provides the channel driver 106-1 associated with Channel 1 with a signal that is representative of the first random frequency F1. In turn, the channel driver 106-1 may amplify the signal and use the amplified signal to drive an associated piezo subarray for a predetermined dwell time. The controller repeats this operation N number of times over the "on" time period. During the "off" time period the controller 104 disables output based on a predetermined duty cycle, e.g., 50%. After the "off" time period the controller 104 continues to execute acts 702-720 in a continuous fashion until otherwise interrupted, e.g., by a shut-off signal or a power loss.

Figure 9:
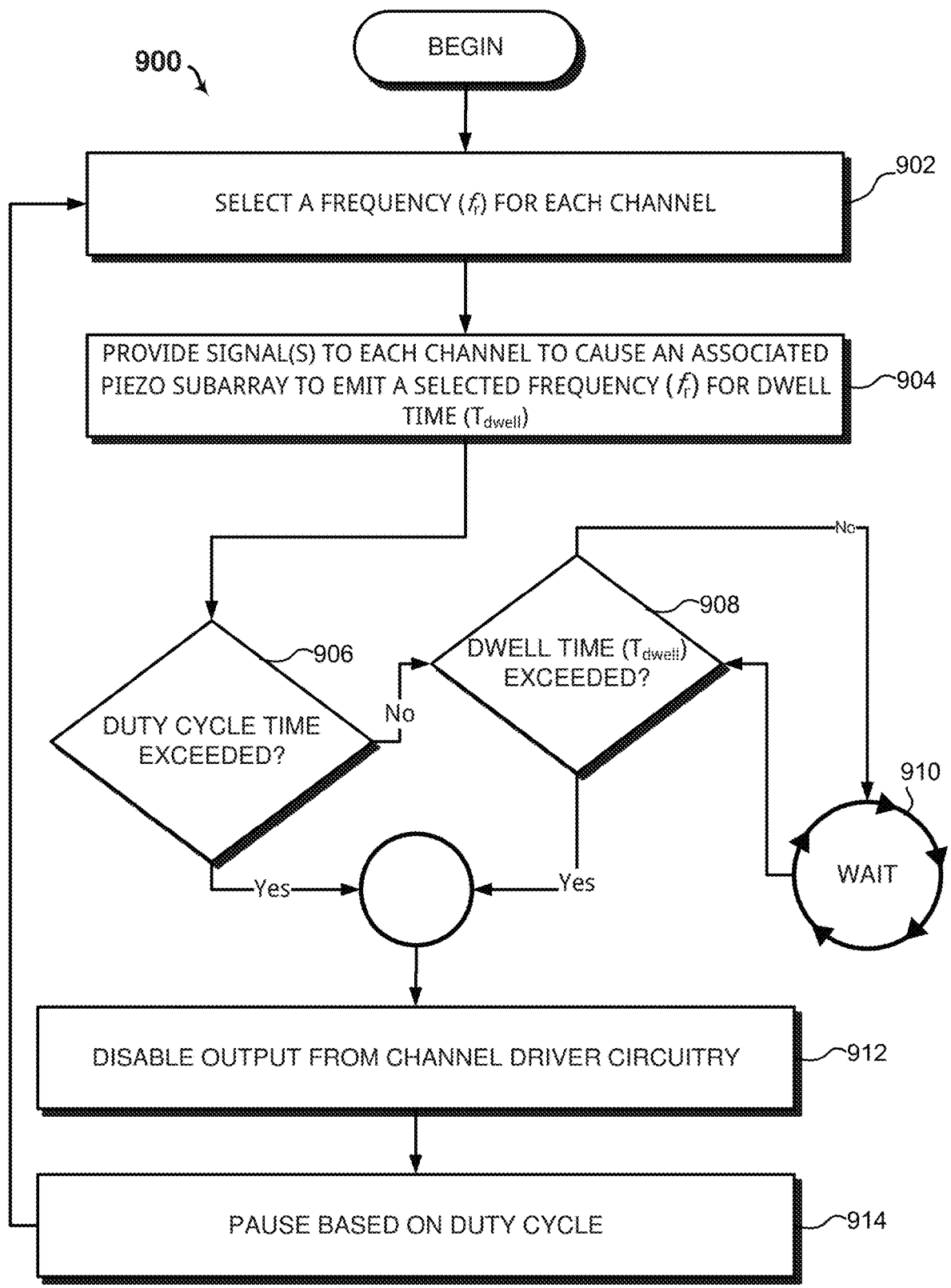
FIG. 9 shows another example process for driving a plurality of piezo sub-arrays to emit colored white noise or to have each piezo sub-array plate emit at a single resonant frequency, in accordance with an embodiment of the present disclosure.

Turning to FIG. 9, another example DU process 900 is shown in accordance with an embodiment of the present disclosure. The process 900 may also include loading operating parameters from a memory, similar to act 702 of FIG. 7, but the description of which will not be repeated for the purpose of brevity.

In act 902, the controller 104 selects a frequency (fr) for each channel. In some cases, the controller 104 operates in a single frequency mode (or a first mode) and simply selects the nominal frequency value for each of the channels. For example, the controller 104 may select 25 kHz for Channel 1, 32 kHz for Channel 2, 40 kHz for Channel 3, and so on. In other cases, the controller 104 operates in a randomized mode (or a second mode) to produce colored white noise. In the randomized mode, the controller 104 selects, for each channel, a random frequency within each respective Channel's upper and lower frequency range.

In act 904, the controller 104 sends a signal to each channel, e.g., via channel driver circuitry 106-1 . . . 106-2, with each respective signal being proportional to the frequency selected for a given channel. For example, in the single frequency mode (or first mode) the controller 104 may send a first signal to Channel 1, e.g., channel driver 106-1, to cause the same to emit at 25 kHz, a second signal to Channel 2, e.g., channel driver 106-2-2, to cause the same to emit at 32 kHz, and so on. In colored white noise mode (or second mode), the controller 104 sends a signal with a selected random frequency to each channel. In any event, the controller 104 may send the signals to each channel at substantially the same time to cause each channel to begin emitting simultaneously. In response, each channel driver, e.g., channel driver circuitry 106-1 . . . 106-6, may cause an associated piezo subarray to emit the selected frequency for the dwell time $T_{dwell}$. As previously discussed, each of the channel driver circuitry 106-1 . . . 106-6 may include amplification/conditioning circuitry to convert the signal from the controller 104 into a proportional electrical signal for driving purposes.

In act 906, if the overall amount of time the controller 104 has driven associated channels is greater than a defined duty cycle time, e.g., 50%, the process 900 continues to act 912. Otherwise, the process 900 continues to act 908. For example, for every 10 seconds of operation the controller 104 may turn channels "on" for 5 seconds and "off" for the other 5 seconds based on a duty cycle of 50%, although this example duty cycle should not be construed as limiting. The controller 104 may utilize a hardware or software timer to measure on/off time.

In act 908, the controller 104 determines if the amount of time the channels are "on" exceeds an associated dwell time. The controller 104 may initiate a timer to determine if the dwell time $T_{dwell}$ has elapsed. If the dwell time $T_{dwell}$ has been exceeded/elapsed, then the process 900 continues to act 912. Otherwise, the process continues to act 910. In act 910, the controller 104 waits for a predetermined amount of time, e.g., a few milliseconds, before returning to act 908.

In act 912, the controller 104 disables output from each channel, e.g., by suspending the signal provided in act 904.

In act 914, the controller 104 pauses for a period of time based on the duty cycle before returning to act 902 and selecting a new random frequency value. As discussed above, the controller 104 may seek to operate the channels at a 50% duty cycle. Therefore, the period of time chosen by the controller 104 to effectively turn "off" the channels may equal that of the total "on" time. For example, if the duty cycle time is 5 seconds then a corresponding off time will be roughly the same, assuming a duty cycle of 50%. Other duty cycles are within the scope of this disclosure and the provided examples are not intended to the limiting.

Figure 10:
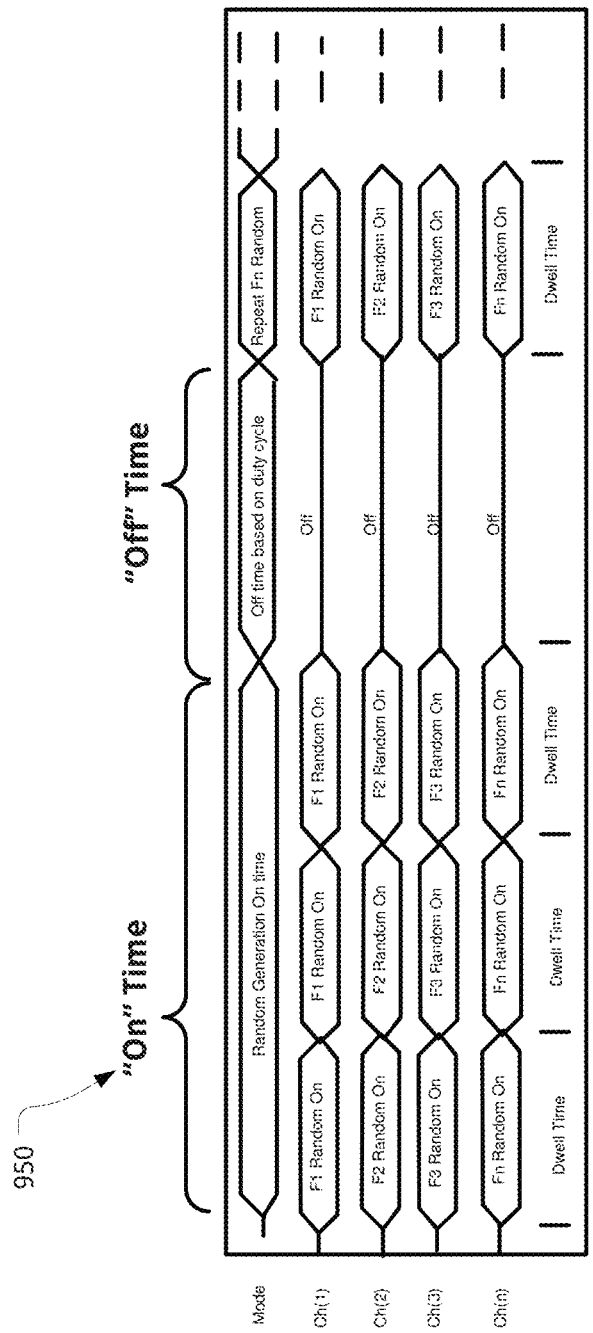
FIG. 10 shows an example timing diagram for a broadband UTD during performance of the example process of FIG. 9.

Turning to FIG. 10, an example timing diagram 950 is shown in accordance with the controller 104 performing the process 900 of FIG. 9. As shown, the controller 104 performs the process 900 in the random mode whereby each channel is driven to emit a random frequency. During the "on" time, the controller 104 provides a signal to each associated channel to cause the same to emit at a selected random frequency. During the "off" time, the controller 104 disables output for a period of time that may be based on an associated duty cycle, as previously discussed. The controller 104 repeats this pattern N times in a continuous fashion to generate a randomized waveform output that substantially approximates colored white noise.

A broadband UTD device configured in accordance with the present disclosure may implement a frequency adjustment process in order to ensure each piezo sub-array is emitting a desired resonant frequency. The present disclosure has identified that a piezo sub-array draws a highest amount of current, e.g., a maximum current, when the same emits a nominal resonant frequency value. During the single frequency mode, as previously discussed with reference to FIG. 9, the broadband UTD 100 may seek to emit at a constant, single-frequency from each piezo sub-array to ensure a maximum SPL is achieved. To this end, a broadband UTD device configured in accordance with the present disclosure may implement a frequency adjustment process that measures a current for each piezo sub-array and increases output frequency for the same until a current measurement drop is detected. In response to detecting the current measurement drop, the broadband UTD device advantageously identifies when a piezo sub-array is outputting at a maximum resonant frequency.

Figure 11:
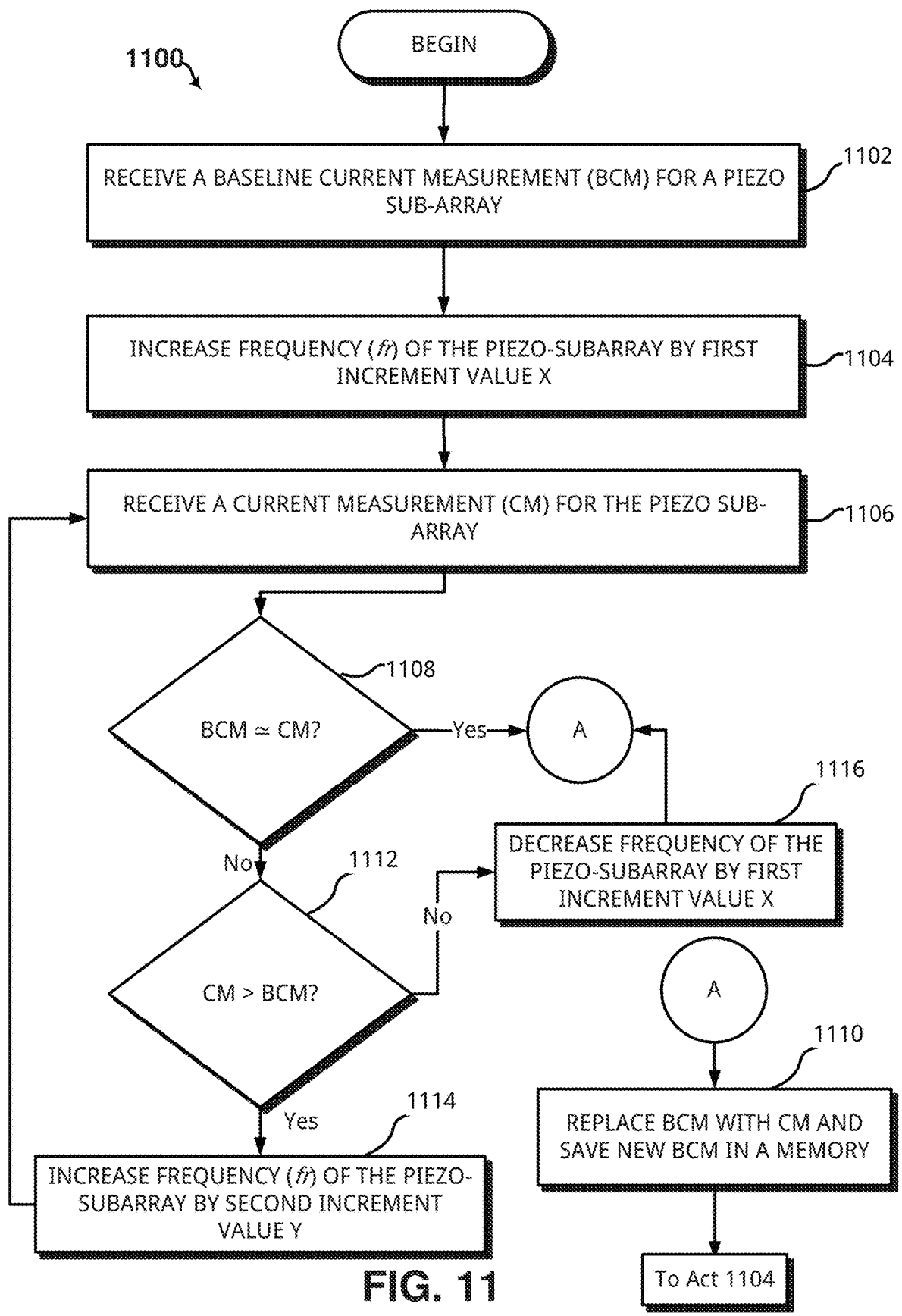
FIG. 11 shows an example process for frequency adjustment by a broadband UTD, in accordance with an embodiment of the present disclosure.

One such example frequency adjustment process 1100 is shown in FIG. 11. The example process 1100 may be implemented by a controller, e.g., controller 104, or any other suitable component of the broadband UTD 100.

In act 1102, the controller 104 receives a baseline current measurement (BCM) for a piezo sub-array, such as the piezo sub-array 409-1, while the piezo sub-array is emitting a particular frequency. The controller 104 may receive the BCM from, for example, the current sensor 105 of FIG. 1. In some cases, the controller 104 may average a number of current measurements (e.g., 5, 10, or 20 measurements) for a given piezo sub-array to establish the BCM. This averaging may reduce noise and increase measurement consistency.

In act 1104, the controller 104 causes an increase in frequency of the piezo sub-array by a first increment value X. The first increment value X may include a resolution of 200 Hz, for example, although other increment values are within the scope of this disclosure. For instance, the controller 104 may increase a drive signal provided to the driver circuitry 106-1 to cause the same to increase a frequency emitted by the piezo sub-array 409-1 in proportion to the first increment value X (e.g., 52 kHz+200 Hz=52.2 kHz).

In act 1106, the controller 104 receives a current measurement (CM) for the piezo-subarray subsequent to increasing the frequency in act 1104. In some cases, the controller 104 receives a plurality of current measurements $CM_0 \ldots CM_N$ associated with the piezo sub-array and averages the same, similar to the averaging of the BCM as discussed above to establish the CM. In any event, and in act 1108, the controller 104 compares the BCM received in act 1102 to the CM received in act 1106. If the BCM substantially equals the CM, e.g., within ±1%, the process 1100 continues to act 1110. Otherwise, the process 1100 continues to act 1112. Note that while the following examples reference a 1% threshold value, other thresholds (e.g., 2%, 5%, 10%, and so on) may be utilized and are also within the scope of this disclosure.

In act 1112, if the CM is greater than the BCM, e.g., CM exceeds the BCM by at least 1% or more, the process continues to act 1114. Otherwise, if the CM is less than the BCM by more than 1%, the process 1100 continues to act 1116. In act 1114, the controller 104 causes an increase in frequency of the piezo sub-array by a second increment value Y. The second increment value Y may include a resolution of 100 Hz, for example, although other increment values are within the scope of this disclosure. For instance, the controller 104 may increase a drive signal provided to the driver circuitry 106-1 to cause the same to increase a frequency emitted by the piezo sub-array 409-1 in proportion to the second increment value Y (e.g., 52.2 kHz+100 Hz=52.3 kHz). In act 1114, the controller 104 also replaces the BCM with the CM and the new BCM is stored in a memory. In act 1110, the controller 104 replaces the BCM with the CM to cause the CM to become the new BCM. The controller 104 may store the new BCM in a memory, for example.

Thus, the process 1100 allows the controller 104 to perform coarse grain frequency adjustment, e.g., by using the first increment value X, and performing subsequent measurements. If the current measured (CM) after such coarse grain adjustment increases by a particular percentage from the baseline (BCM), the controller 104 proceeds to increase frequency in a fine-grain manner by using the second increment value Y, with value Y being less than increment value X. Each time a subsequent current measurement increases from a measurement previous to an adjustment, the controller 104 has, in a general sense, "edged" closer to the nominal resonant frequency. This fine-grain increase of frequency continues N number of times until a current drop is detected. In the event a current drop is detected, the controller 104 identifies that the nominal resonant frequency has been exceeded and performs a correction by decreasing frequency by the increment value X.

In accordance with an aspect of the present disclosure a broadband ultrasonic transducer device (UTD) is disclosed. The broadband UTD comprising a plurality of piezo sub-array plates coupled to a base portion, each of the piezo sub-array plates being associated with a nominal resonant frequency and including a plurality of openings to receive a piezo electric transducer element, and a plurality of piezo electric transducer elements each coupled to a respective opening of the plurality of openings, driver circuitry electrically coupled to each of the plurality of piezo sub-array plates, the driver circuitry configured to cause each of the piezo sub-array plates to emit ultrasonic energy based on the nominal resonant frequency associated with each piezo sub-array plate.

In accordance with another aspect of the present disclosure a broadband ultrasonic transducer device (UTD) is disclosed. The broadband UTD comprising a plurality of piezo sub-array plates coupled to a base portion, each of the piezo sub-array plates being associated with a nominal resonant frequency and including a plurality of openings to receive a piezo electric transducer element, a plurality of piezo electric transducer elements each coupled to a respective opening of the plurality of openings, each piezo electric transducer element being a narrow-band transducer device, driver circuitry electrically coupled to each of the plurality of piezo sub-array plates, the driver circuitry configured to cause each of the piezo sub-array plates to emit ultrasonic energy based on the nominal resonant frequency associated with each piezo sub-array plate, and a controller electrically coupled to the driver circuitry and configured cause the plurality of piezo sub-array plates to emit a pattern of ultra-sonic energy based at least in part on a control scheme.

In accordance with yet another aspect of the present disclosure a method of driving a plurality of piezo sub-array plates to emit a pattern of ultra-sonic energy is disclosed. The method comprising selecting, by a controller, a first frequency for at least a first piezo sub-array plate, the first piezo sub-array plate having a plurality of openings and a plurality of narrow-band piezo electric transducer elements coupled to a respective opening of the plurality of openings, wherein the first piezo sub-array plate is associated with a first nominal resonant frequency based at least in part on the plurality of openings, and providing, by the controller, a first signal representing the selected first frequency to channel driver circuitry associated with the first piezo sub-array plate, the first signal being configured to cause the channel driver circuitry to drive the first piezo sub-array plate at the selected first frequency.

Embodiments of the methods described herein may be implemented using a processor and/or other programmable device. To that end, the methods described herein may be implemented on a tangible computer readable medium having instructions stored thereon that when executed by one or more processors perform the methods. Thus, for example, controller 104 may include a storage medium (not shown) to store instructions (in, for example, firmware or software) to perform the operations described herein. The storage medium may include any type of tangible medium, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of media suitable for storing electronic instructions.

Elements, components, modules, and/or parts thereof that are described and/or otherwise portrayed through the figures to communicate with, be associated with, and/or be based on, something else, may be understood to so communicate, be associated with, and/or be based on in a direct and/or indirect manner, unless otherwise stipulated herein.

Throughout the entirety of the present disclosure, use of the articles "a" and/or "an" and/or "the" to modify a noun may be understood to be used for convenience and to include one, or more than one, of the modified noun, unless otherwise specifically stated. The terms "comprising", "including" and "having" are intended to be inclusive and mean that there may be additional elements other than the listed elements. As used herein, use of the term "nominal" or "nominally" when referring to an amount means a designated or theoretical amount that may vary from the actual amount.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Also features of any embodiment described herein may be combined or substituted for features of any other embodiment described herein.

While the principles of the disclosure have been described herein, it is to be understood by those skilled in the art that this description is made only by way of example and not as a limitation as to the scope of the disclosure. Other embodiments are contemplated within the scope of the present disclosure in addition to the embodiments shown and described herein. Modifications and substitutions by one of ordinary skill in the art are considered to be within the scope of the present disclosure, which is not to be limited except by the following claims.

What is claimed is:

1. A broadband ultrasonic transducer device (UTD), comprising:
   a plurality of piezo sub-array plates coupled to a base portion, each of the piezo sub-array plates being associated with a different nominal resonant frequency and including a plurality of openings to receive a piezo electric transducer element, and a plurality of piezo electric transducer elements each coupled to a respective opening of the plurality of openings; and
   driver circuitry electrically coupled to each of the plurality of piezo sub-array plates, the driver circuitry configured to cause each of the piezo sub-array plates to emit ultrasonic energy based on the nominal resonant frequency associated with each piezo sub-array plate.

2. The broadband (UTD) of claim 1, wherein the nominal resonant frequency associated with each piezo sub-array plate of the plurality of piezo sub-array plates is based on the following equations:

$$RFreq = \alpha\left(\frac{h}{rdisk^2}\right)$$

$$\alpha = 0.412\left(\sqrt{\left(\frac{Y}{0.91\rho}\right)}\right)$$

wherein $\alpha$ is an approximation of compressibility of a material of a bending element, h is a thickness of the bending element, Y is Young's Modulus, p is a density of ceramic material, and rdisk is a radius of the bending element.

3. The broadband UTD of claim 1, wherein each of the plurality of piezo electric transducer elements comprise enclosed-type transducer devices.

4. The broadband UTD of claim 1, wherein each of the piezo sub-array plates is associated with a different resonant frequency.

5. The broadband UTD of claim 1, wherein each of the piezo sub-array plates is associated with a resonant frequency ranging between 20 kHz and 100 kHz.

6. The broadband UTD of claim 1, wherein each piezo electric transducer element is coupled to a respective opening based at least in part on an adhesive.

7. The broadband UTD of claim 6, wherein each opening of the plurality of openings includes a first diameter, the first diameter being larger than a diameter of each of the piezo electric transducer elements.

8. The broadband UTD of claim 6, wherein each of the plurality of piezo electric transducer elements include a diameter D, and wherein each opening of the plurality of openings includes a diameter substantially equal to that of the diameter D to receive a respective piezo electric transducer element.

9. The broadband UTD of claim 1, wherein each piezo sub-array plate comprises an electrically conductive material, and wherein each piezo electric transducer element of a respective piezo sub-array plate is in electrical communication with associated driver circuitry based at least in part on the electrically conductive material.

10. The broadband UTD of claim 1, wherein each piezo electric transducer element electrically couples to associated driver circuitry via a flexible conductive fabric.

11. The broadband UTD of claim 10, wherein each the flexible conductive fabric couples to an associated piezo electric transducer element via an adhesive.

12. The broadband UTD of claim 1, wherein each piezo electric transducer element emits a beam angle radiation pattern of about 30 degrees, and wherein the plurality of piezo sub-array plates collectively emit a beam angle radiation pattern up to about 90 degrees.

13. A broadband ultrasonic transducer device (UTD), comprising:
a plurality of piezo sub-array plates coupled to a base portion, each of the piezo sub-array plates being associated with a different nominal resonant frequency and including a plurality of openings to receive a piezo electric transducer element, and a plurality of piezo electric transducer elements each coupled to a respective opening of the plurality of openings, each piezo electric transducer element being a narrow-band transducer device;
driver circuitry electrically coupled to each of the plurality of piezo sub-array plates, the driver circuitry configured to cause each of the piezo sub-array plates to emit ultrasonic energy based on the nominal resonant frequency associated with each piezo sub-array plate; and
a controller electrically coupled to the driver circuitry and configured cause the plurality of piezo sub-array plates to emit a pattern of ultra-sonic energy based at least in part on a control scheme.

14. The broadband (UTD) of claim 13, wherein the nominal resonant frequency associated with each piezo sub-array plate of the plurality of piezo sub-array plates is based on the following equations:

$$RFreq = \alpha\left(\frac{h}{rdisk^2}\right)$$

$$\alpha = 0.412\left(\sqrt{\left(\frac{Y}{0.91\rho}\right)}\right)$$

wherein $\alpha$ is an approximation of compressibility of a material of a bending element, h is a thickness of the bending element, Y is Young's Modulus, p is a density of ceramic material, and rdisk is a radius of the bending element.

15. The broadband UTD of claim 13, wherein the pattern of ultra-sonic energy approximates white noise.

16. A method of driving a plurality of piezo sub-array plates each having a different nominal resonant frequency to emit a pattern of ultra-sonic energy, the method comprising:
selecting, by a controller, a first frequency for at least a first piezo sub-array plate, the first piezo sub-array plate having a plurality of openings and a plurality of narrow-band piezo electric transducer elements coupled to a respective opening of the plurality of openings, wherein the first piezo sub-array plate is associated with a first nominal resonant frequency based at least in part on the plurality of openings; and
providing, by the controller, a first signal representing the selected first frequency to channel driver circuitry associated with the first piezo sub-array plate, the first signal being configured to cause the channel driver circuitry to drive the first piezo sub-array plate at the selected first frequency.

17. The method of claim 16, further comprising:
selecting, by the controller, a second frequency for at least a second piezo sub-array plate, the second piezo sub-array plate having a plurality of openings and a plurality of narrow-band piezo electric transducer elements coupled to a respective opening of the plurality of openings, wherein the second piezo sub-array plate is associated with a second nominal resonant frequency based at least in part on the plurality of openings; and
providing, by the controller, a second signal representing the selected second frequency to channel driver circuitry associated with the second piezo sub-array plate, the second signal being configured to cause the channel driver circuitry to drive the second piezo sub-array plate at the selected second frequency.

18. The method of claim 17, wherein the controller provides the first and second signal to channel driver circuitry associated with the first and second piezo sub-array plate, respectively, in a substantially simultaneous fashion.

19. The method of claim 16, wherein selecting the first frequency for at least the first piezo sub-array plate further comprises selecting a random frequency based on the first nominal resonant frequency associated with the first piezo sub-array.

20. The method of claim 16, further comprising receiving a current measurement for the first piezo sub-array, and wherein providing the first signal to the channel driver circuitry associated with the first piezo sub-array plate further comprises adjusting the first signal based at least in part on the current measurement.

* * * * *